United States Patent
Mannick et al.

(10) Patent No.: US 10,993,940 B2
(45) Date of Patent: May 4, 2021

(54) METHODS OF ENHANCING IMMUNE RESPONSE

(71) Applicant: NOVARTIS AG, Basel (CH)

(72) Inventors: Joan Mannick, Weston, MA (US); Melody Morris, Boston, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/592,293

(22) Filed: Oct. 3, 2019

(65) Prior Publication Data

US 2020/0061051 A1 Feb. 27, 2020

Related U.S. Application Data

(62) Division of application No. 15/821,229, filed on Nov. 22, 2017, now Pat. No. 10,441,584.

(60) Provisional application No. 62/425,766, filed on Nov. 23, 2016, provisional application No. 62/476,160, filed on Mar. 24, 2017, provisional application No. 62/576,511, filed on Oct. 24, 2017.

(51) Int. Cl.
| | |
|---|---|
| *A61K 31/4745* | (2006.01) |
| *A61P 13/02* | (2006.01) |
| *A61P 31/12* | (2006.01) |
| *A61P 1/02* | (2006.01) |
| *A61P 11/00* | (2006.01) |
| *A61K 31/436* | (2006.01) |
| *A61P 31/00* | (2006.01) |
| *A61P 31/16* | (2006.01) |

(52) U.S. Cl.
CPC ........ *A61K 31/4745* (2013.01); *A61K 31/436* (2013.01); *A61P 1/02* (2018.01); *A61P 11/00* (2018.01); *A61P 13/02* (2018.01); *A61P 31/00* (2018.01); *A61P 31/12* (2018.01); *A61P 31/16* (2018.01)

(58) Field of Classification Search
CPC .............. A61K 2300/00; A61K 31/436; A61K 31/4745; A61P 11/00; A61P 13/02; A61P 1/02; A61P 31/00; A61P 31/12; A61P 31/16
See application file for complete search history.

(56) References Cited

U.S. PATENT DOCUMENTS

| | | |
|---|---|---|
| 3,929,992 A | 12/1975 | Sehgal et al. |
| 5,665,772 A | 9/1997 | Cottens et al. |
| 5,741,677 A | 4/1998 | Kozlowski et al. |
| 6,015,815 A | 1/2000 | Mollison |
| 6,440,458 B1 | 8/2002 | Yamashita et al. |
| 7,091,213 B2 | 8/2006 | Metcalf, III et al. |
| 7,667,039 B2 | 2/2010 | Garcia-Echeverria et al. |
| 7,994,170 B2 | 8/2011 | Garcia-Echeverria et al. |

(Continued)

FOREIGN PATENT DOCUMENTS

| | | |
|---|---|---|
| CN | 1195289 A | 10/1998 |
| CN | 101862297 A | 10/2010 |

(Continued)

OTHER PUBLICATIONS

Araki et al., "The role of mTOR in memory of CD8+ T-cell differentiation," Immunol Rev., 235(1):234-243 (2010).

(Continued)

*Primary Examiner* — Savitha M Rao
(74) *Attorney, Agent, or Firm* — Andrea L. C. Reid; Danielle M. Nihan; Dechert LLP

(57) ABSTRACT

The present invention relates to a method of enhancing immune response in a subject.

24 Claims, 5 Drawing Sheets

(56) References Cited

U.S. PATENT DOCUMENTS

| | | | |
|---|---|---|---|
| 8,431,592 B2 | 4/2013 | Garcia-Echeverria et al. |
| 8,436,177 B2 | 5/2013 | Stowasser et al. |
| RE44,768 E | 2/2014 | Skotnicki et al. |
| 9,358,229 B2 | 6/2016 | Vannucchi et al. |
| 9,358,236 B2 | 6/2016 | Murphy et al. |
| 9,370,508 B2 | 6/2016 | Garcia-Echeverria et al. |
| 10,004,803 B2 | 6/2018 | Mannick et al. |
| 10,286,069 B2 | 5/2019 | Mannick et al. |
| 10,441,584 B2 | 10/2019 | Mannick et al. |
| 2004/0228917 A1 | 11/2004 | Oshlack et al. |
| 2005/0101624 A1 | 5/2005 | Betts et al. |
| 2006/0264453 A1 | 11/2006 | Mudumba et al. |
| 2007/0036857 A1 | 2/2007 | Becker |
| 2007/0265294 A1 | 11/2007 | Kleinman |
| 2008/0206322 A1 | 8/2008 | Becker |
| 2009/0082387 A1 | 3/2009 | Czarnik |
| 2009/0088373 A1 | 4/2009 | Gallo et al. |
| 2009/0270515 A1 | 10/2009 | Gruber |
| 2010/0129357 A1 | 5/2010 | Garcia-Martinez |
| 2010/0150829 A1 | 6/2010 | Garcia-Martinez |
| 2010/0152147 A1 | 6/2010 | Fuge et al. |
| 2010/0196311 A1 | 8/2010 | Kim et al. |
| 2010/0196365 A1 | 8/2010 | Garcia-Echeverria et al. |
| 2010/0233733 A1 | 9/2010 | Fantl |
| 2010/0260858 A1 | 10/2010 | Ruddy |
| 2011/0020338 A1 | 1/2011 | Garcia-Echeverria et al. |
| 2011/0129496 A1 | 6/2011 | Ahmed et al. |
| 2011/0230476 A1 | 9/2011 | Niu et al. |
| 2012/0148552 A1 | 6/2012 | Jensen |
| 2012/0207751 A1 | 8/2012 | Garcia-Echeverria et al. |
| 2012/0282252 A1 | 11/2012 | Garcia-Echeverria et al. |
| 2013/0178479 A1 | 7/2013 | Chen et al. |
| 2013/0245061 A1 | 9/2013 | Cao et al. |
| 2013/0289064 A1 | 10/2013 | Stowasser et al. |
| 2013/0296316 A1 | 11/2013 | Pollastri et al. |
| 2013/0309258 A1 | 11/2013 | June |
| 2014/0206678 A1 | 7/2014 | Shenk et al. |
| 2014/0242162 A1 | 8/2014 | Diederich et al. |
| 2014/0243396 A1 | 8/2014 | Griffin et al. |
| 2015/0000744 A1 | 1/2015 | Park et al. |
| 2015/0051266 A1 | 2/2015 | Kochenderter |
| 2015/0079155 A1 | 3/2015 | Jensen |
| 2015/0140036 A1 | 5/2015 | Mannick et al. |
| 2015/0157645 A1 | 6/2015 | Hirawat et al. |
| 2016/0045441 A1 | 2/2016 | Diederich et al. |
| 2016/0046724 A1 | 2/2016 | Brogdon |
| 2016/0051651 A1 | 2/2016 | Brogdon |
| 2016/0068601 A1 | 3/2016 | Brogdon |
| 2016/0096892 A1 | 4/2016 | Brogdon |
| 2017/0049754 A1 | 2/2017 | Diederich et al. |
| 2017/0274014 A1 | 9/2017 | Brogdon et al. |
| 2017/0281753 A1 | 10/2017 | Mannick et al. |
| 2017/0304293 A1 | 10/2017 | Smallwood et al. |
| 2018/0161280 A1 | 6/2018 | Diederich et al. |
| 2018/0289694 A1 | 10/2018 | Glass et al. |

FOREIGN PATENT DOCUMENTS

| | | |
|---|---|---|
| CN | 101969931 A | 2/2011 |
| CN | 102138903 A | 8/2011 |
| CN | 102199152 | 9/2011 |
| CN | 102292078 A | 12/2011 |
| DE | 2347682 | 4/1974 |
| EP | 0868911 | 10/1998 |
| JP | H11509223 | 8/1999 |
| JP | 2003530340 | 10/2003 |
| JP | 2004035547 | 2/2004 |
| JP | 2004354394 A | 12/2004 |
| JP | 2006188539 A | 7/2006 |
| JP | 2009102341 | 5/2009 |
| TW | 550091 B | 9/2003 |
| WO | WO 9409010 | 4/1994 |
| WO | WO 9514023 | 5/1995 |
| WO | WO 9516691 | 6/1995 |
| WO | WO 9641807 | 12/1996 |
| WO | WO 9802441 | 1/1998 |
| WO | WO 9915530 | 4/1999 |
| WO | WO 0114387 | 3/2001 |
| WO | WO 2005034916 A1 | 4/2005 |
| WO | WO 2006094507 | 9/2006 |
| WO | WO 2006122806 A2 | 11/2006 |
| WO | WO 2008016633 A2 | 2/2008 |
| WO | WO 2008064093 | 5/2008 |
| WO | WO 2008103636 A1 | 8/2008 |
| WO | WO 2009013305 A1 | 1/2009 |
| WO | WO 2009118324 A1 | 10/2009 |
| WO | WO 2010056754 A2 | 5/2010 |
| WO | WO 2010049481 A1 | 6/2010 |
| WO | WO 2010118419 A2 | 10/2010 |
| WO | WO 2010129622 A1 | 11/2010 |
| WO | WO 2011031896 A2 | 3/2011 |
| WO | WO 2012006619 A2 | 1/2012 |
| WO | WO 2012047775 A1 | 4/2012 |
| WO | WO 2012075253 A2 | 6/2012 |
| WO | WO 2012103524 A2 | 8/2012 |
| WO | WO 2012110953 A1 | 8/2012 |
| WO | WO 2013023119 A1 | 2/2013 |
| WO | WO 2013049300 A1 | 4/2013 |
| WO | WO 2013050419 A1 | 4/2013 |
| WO | WO 2013184621 A2 | 12/2013 |
| WO | WO 2014137946 A1 | 9/2014 |
| WO | WO 2014147567 | 9/2014 |
| WO | WO 20140191128 A1 | 12/2014 |
| WO | WO 2015073644 A1 | 5/2015 |
| WO | WO 2015188119 | 12/2015 |
| WO | WO 2016014530 A1 | 1/2016 |
| WO | WO 2016064683 A1 | 4/2016 |
| WO | WO 2016079332 A1 | 5/2016 |
| WO | WO 2016185443 | 11/2016 |
| WO | WO 2018096402 A1 | 5/2018 |

OTHER PUBLICATIONS

Ballou et al., "Rapamycin and mTOR kinase inhibitors," J Chem Biol., Nov. 2008, vol. 1(1-4), pp. 27-36. doi: 10.1007/s12154-008-0003-5. Epub May 15, 2008.

Berg et al., "The role of CD8 T cells in innate immunity and in antigen non-specific protection," Current Opinion in Immunology, vol. 18, pp. 338-343 (2006).

Bitto et al., "Transient rapamycin treatment can increase lifespan and healthspan in middle-aged mice," Elife, Aug. 23, 2016, 5:e16351. doi: 10.7554/eLife.16351.

Boraschi et al., "The Gracefully Aging Immune System," Sci Transl Med, 2013, vol. 5, No. 185, ps8.

Cai et al., "Rapamycin, Autophagy, and Alzheimer's Disease," Journal of Biochemical and Pharmacological Research, vol. 1, No. 2, Jun. 2013 (pp. 84-90).

Chen et al., "mTOR regulation and therapeutic rejuvenation of aging hematopoietic stem cells," Sci Signal, 2009, vol. 2, No. 98, ra75.

Chi, "Regulation and function of mTOR signalling in T cell fate decisions," Nature Reviews immunology, vol. 12, No. 5, Apr. 2012 (pp. 325-338).

Clegg et al., "Frailty in elderly people," Lancet, Mar. 2, 2013, vol. 381, No. 9868, pp. 752-762. doi: 10.1016/ S0140-6736(12)62167-9. Epub Feb. 8, 2013. Review. Erratum in: Lancet. Oct. 19, 2013;382(9901):1328.

Dello Russo et al., "Involvement of mTOR kinase in cytokine-dependent microglial activation and cell proliferation," Biochemical Pharmacology, 2009, vol. 78, No. 9, pp. 1242-1251.

Dominick et al., "Regulation of mTOR activity in Snell dwarf and GH receptor gene-disrupted mice," Endocrinology, Feb. 2015, vol. 156, No. 2, pp. 565-575. doi: 10.1210/en.2014-1690. Epub Dec. 2, 2014.

Ewald et al., "Dauer-independent insulin/IGF-1-signalling implicates collagen remodelling in longevity," Nature, Mar. 5, 2015, vol. 519, No. 7541, pp. 97-101.

Feldman et al., "Active-site inhibitors of mTOR target rapamycin-resistant outputs of mTORC1 and mTORC2," PLoS Biol., Feb. 10, 2009, vol. 7, No. 2, p. e38 (13 pages).

(56) References Cited

OTHER PUBLICATIONS

Flynn et al., "Late-life rapamycin treatment reverses age-related heart dysfunction," Aging Cell, 2013, vol. 12, pp. 851-862.
Golden-Mason et al., "Upregulation of PD-1 Expression on Circulating and Intrahepatic Hepatitis C Virus-Specific CD8+ T Cells Associated with Reversible Immune Dysfunction," Journal of Virology, Sep. 2007, vol. 81, No. 17, pp. 9249-9258.
Harari et al., "A robust type I interferon gene signature from blood RNA defines quantitative but not qualitative differences between three major IFNβ drugs in the treatment of multiple sclerosis," Hum Mol Genet., Jun. 1, 2015, vol. 24, No. 11, pp. 3192-3205. doi: 10.1093/hmg/ddv071.
Harrison et al., "Rapamycin fed late in life extends lifespan in genetically heterogeneous mice," Nature, vol. 406, No. 7253, Jul. 2009 (pp. 392-395).
Huye et al., "Combining mTor inhibitors with rapamycin-resistant T cells: a two-pronged approach to tumor elimination," Mol Ther., Dec. 2011, vol. 19, No. 12, pp. 2239-2248. Epub Aug. 30, 2011.
International Search Report and Written Opinion dated Jun. 13, 2012 in connection with International Application No. PCT/IB2012/050669.
International Search Report and Written Opinion dated Dec. 10, 2012 in connection with International Application No. PCT/EP2012/069541.
International Search Report and Written Opinion dated Jun. 23, 2014 in connection with Application No. PCT/IB2014/059965.
International Search Report and Written Opinion dated May 6, 2015 in connection with Application No. PCT/US2014/065408.
International Search Report and Written Opinion dated Sep. 16, 2016 in connection with Application No. PCT/IB2016/052980.
International Search Report and Written Opinion dated Mar. 12, 2018 in connection with Application No. PCT/IB2017/001579.
Iob et al., "Evidence of increased clinical protection of an MF59-adjuvant influenza vaccine compared to a non-adjuvant vaccine among elderly residents of long-term care facilities in Italy," Epidemiol. Infect., 2005, vol. 133, pp. 687-693.
Keating et al., Nat Immunol. Dec. 2013;14(12):1266-76. Epub Oct. 20, 2013.
Kumar et al., "Age-related decline in immunity: implications for vaccine responsiveness," Expert Rev Vaccines, vol. 7, No. 4, pp. 467-479.
Lamming et al., "Depletion of Rictor, an essential protein component of mTORC2, decreases male lifespan," Aging Cell, 2014, vol. 13, pp. 911-917.
Lamming et al., "Rapamycin-induced insulin resistance is mediated by mTORC2 loss and uncoupled from longevity," Science, 2012, vol. 335, pp. 1638-1643.
Laplante et al., "mTOR signaling in growth control and disease," Cell, 2012, vol. 149, pp. 274-293.
Lichterfeld et al., "Telomerase activity of HIV-1-specific CD8+ T cells: constitutive up-regulation in controllers and selective increase by blockade of PD ligand 1 in progressors," Blood, 2008, vol. 112, No. 9, pp. 3679-3687.
Lievesley, Ed., "Ageism and age discrimination in secondary health care in the United Kingdom: A review of the literature," Department of Health, Centre for Policy on Ageing. Dec. 2009.
Mannick et al., "mTOR inhibition improves immune function in the elderly," Science Translational Medicine, Dec. 24, 2014, vol. 6, No. 268, pp. 268ra179.

McMichael et al., "Influenza vaccines: mTOR inhibition surprisingly leads to protection," Nat Immunol., Dec. 2013, vol. 14, No. 12, pp. 1205-1207.
McNab, et al., "Type I interferons in infectious disease," Nat Rev Immunol., Feb. 2015, vol. 15, No. 2, pp. 87-103. doi: 10.1038/nri3787. Review.
Murray et al., Antivir Chem Chemother., 22(5):205-215 (2012).
Nunes et al., "Expansion of a CD8+PD-1+ Replicative Senescence Phenotype in Early Stage CLL Patients is Associated with Inverted CD4:CD8 Ratios and Disease Progression," Human Cancer Research, 2012, Clinical Cancer Research, vol. 18, No. 3, pp. 678-687.
Nyfeler et al., "RAD001 enhances the potency of BEZ235 to inhibit mTOR signaling and tumor growth," PLoS One, 2012, vol. 7, No. 11, pp. e48548. doi: 10.1371/journal.pone.0048548. Epub Nov. 14, 2012.
Nyfeler et al., "Relieving autophagy and 4EBP1 from rapamycin resistance," Mol Cell Biol., Jul. 2011, vol. 31, No. 14, pp. 2867-2876. doi: 10.1128/MCB.05430-11. Epub May 16, 2011.
Passacantilli et al., "Combined Therapy with RAD001 e BEZ235 overcomes resistance of PET immortalized cell lines to mTOR inhibition," Oncotarget, Jul. 30, 2014, vol. 5, No. 14, pp. 5381-5391.
Pollizzi et al., "Equivalent benefit of mTORCI blockade and combined PI3K-mTOR blockade in a mouse-model of tuberous sclerosis," Molecular Cancer, 2009, vol. 8, No. 38, pp. 1-9.
Sarkar et al., "A rational mechanism for combination treatment of Huntington's disease using lithium and rapamycin," Human Molecular Genetics, 2008, vol. 17, No. 2, pp. 170-178.
Sarkar et al., "Rapamycin and mTOR-independent autophagy inducers ameliorate toxicity of polyglutamine-huntingtin and related proteinopathies." Cell and Death Differentiation, 2009, vol. 16, pp. 46-56.
Serra et al., "NVP-BEZ235, a dual PI3K/mTOR inhibitor, prevents PI3K signaling and inhibits the growth of cancer cells with activating PI3K mutations," Cancer Res., Oct. 1, 2008, vol. 68, No. 19, pp. 8022-8030. doi: 10.1158/0008-5472.CAN-08-1385.
Shimatani et al., "PD-1+ memory phenotype CD4+ T cells expressing C/EBP underlie T cell immunodepression in senescence and leukemia," PNAS, Sep. 15, 2009, vol. 106, No. 37, pp. 15807-15812.
United States Securities and Exchange Commission "Form 8-K: Current Report Pursuant to Section 13 or 15(d) of the Securities Exchange Act of 1934: Restorbio, Inc." Jul. 25, 2018.
U.S. Appl. No. 16/361,822 of Mannick et al., filed Mar. 22, 2019.
Watanabe et al., Abstract A167, Molecular cancer therapeutics, Nov. 2013 pp. 1-2.
Weinberger et al., "Biology of Immune Responses to Vaccines in Elderly Persons," Clinical Infectious Diseases, vol. 46, pp. 1078-1084 (2008).
Wilkinson et al., "Rapamycin slows aging in mice," Aging Cell, vol. 11, No. 4, Aug. 2012 (pp. 675-682).
Withers et al., "S6 Kinase and Ageing," Abstract, British Society for Research on Ageing, Annual Scientific Meeting. Sep. 2-4, 2013. University of East Anglia, Norwich.
Zhang et al., "Aging Leads to Disturbed Homeostasis of Memory Phenotype CD8+ Cells," J. Exp. Med., vol. 195, No. 3, pp. 283-293 (2002).
Zhou et al., "Updates of mTOR inhibitors," Anticancer Agents Med Chem., Sep. 2010, vol. 10, No. 7, pp. 571-581.

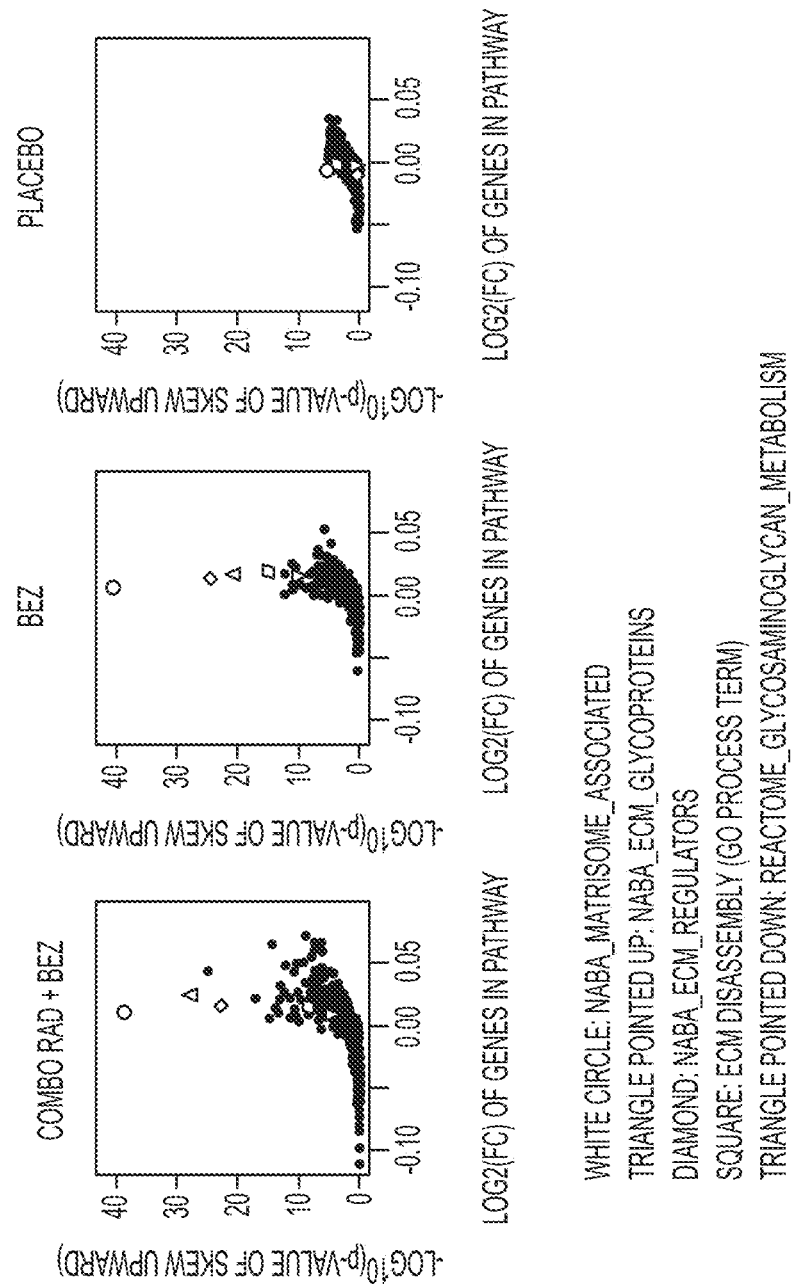

METHODS OF ENHANCING IMMUNE RESPONSE

CROSS-REFERENCE TO RELATED PATENT APPLICATIONS

This application is a Division of U.S. application Ser. No. 15/821,229, filed Nov. 22, 2017, which claims the benefit of priority to U.S. Provisional Patent Application No. 62/425,766, filed Nov. 23, 2016; U.S. Provisional Patent Application No. 62/476,160, filed Mar. 24, 2017; and U.S. Provisional Patent Application No. 62/576,511, filed Oct. 24, 2017, the contents of each of which are incorporated herein by reference.

FIELD OF THE INVENTION

The present invention relates to (a) RAD001, or a pharmaceutically acceptable salt thereof; (b) BEZ235, or a pharmaceutically acceptable salt thereof; or (c) a combination thereof, for simultaneous, separate or sequential use for promotion and/or enhancement of an immune response in a subject; a pharmaceutical composition comprising such combination; a method of promoting and/or enhancing an immune response in a subject comprising administration of said RAD001 or BEZ235 or combination to a subject in need thereof; use of same for preparation of a medicament for the promotion and/or enhancement of an immune response in a subject; and a commercial package thereto.

BACKGROUND OF THE INVENTION mTOR is an evolutionarily conserved serine/threonine kinase that plays a central role in integrating environmental cues in the form of growth factors, amino acids, and energy. In the study of the immune system, mTOR is emerging as a critical regulator of immune function because of its role in sensing and integrating cues from the immune microenvironment. With the greater appreciation of cellular metabolism as an important regulator of immune cell function, mTOR is proving to be a vital link between immune function and metabolism. mTOR has the ability to direct the adaptive immune response, e.g. promoting differentiation, activation, and function in T cells, B cells, and antigen-presenting cells.

SUMMARY OF THE INVENTION

In one aspect, the present invention relates to a method comprising the step of administering (a) a low dose of RAD001 or a pharmaceutically acceptable salt thereof; (b) a low dose of BEZ235 or a pharmaceutically acceptable salt thereof; or (c) a combination thereof, to a patient, wherein the patient experiences fewer illnesses due to infection than a patient not administered RAD001 or a pharmaceutically acceptable salt thereof, BEZ235 or a pharmaceutically acceptable salt thereof, or a combination thereof.

In another aspect, the present invention relates to (a) RAD001, or a pharmaceutically acceptable salt thereof; (b) BEZ235, or a pharmaceutically acceptable salt thereof; or (c) a combination thereof for simultaneous, separate or sequential use for the promotion and/or enhancement of an immune response in a subject.

In one aspect, the invention provides a pharmaceutical composition comprising (a) RAD001, or a pharmaceutically acceptable salt thereof; (b) BEZ235, or a pharmaceutically acceptable salt thereof; or (c) a combination thereof. In some embodiments, BEZ235, or a pharmaceutically acceptable salt thereof, is effective at promoting and/or enhancing an immune response in a subject, such as innate immunity. In some embodiments, the combination is jointly therapeutically effective at promoting and/or enhancing an immune response in a subject.

In one aspect, the present invention provides a method of promoting and/or enhancing an immune response in subject comprising administering to subject in need thereof (a) RAD001, or a pharmaceutically acceptable salt thereof; (b) BEZ235, or a pharmaceutically acceptable salt thereof; or (c) a combination thereof in an amount effective at promoting and/or enhancing said immune response.

In one aspect, the present invention also provides a method of treating an age-related condition, comprising administering to a subject in need thereof an effective amount of (a) RAD001, or a pharmaceutically acceptable salt thereof; (b) BEZ235, or a pharmaceutically acceptable salt thereof; or (c) a combination thereof to treat said age-related condition.

In one aspect, the present invention provides the use of (a) RAD001, or a pharmaceutically acceptable salt thereof; (b) BEZ235, or a pharmaceutically acceptable salt thereof; or (c) a combination thereof for the promotion and/or enhancement of an immune response in a subject, and for the preparation of a medicament for the promotion and/or enhancement of an immune response.

In one aspect, the present invention provides the use of (a) RAD001, or a pharmaceutically acceptable salt thereof; (b) BEZ235, or a pharmaceutically acceptable salt thereof; or (c) a combination thereof for the treatment of an age-related condition in a subject.

In one aspect, the present invention provides a commercial package comprising as active ingredients (a) RAD001, or a pharmaceutically acceptable salt thereof; (b) BEZ235, or a pharmaceutically acceptable salt thereof; or (c) a combination thereof, together with instructions for the simultaneous, separate or sequential use thereof in the promotion and/or enhancement of an immune response in a subject.

In one aspect, the present invention provides a commercial package comprising (a) RAD001, or a pharmaceutically acceptable salt thereof and instructions for the simultaneous, separate or sequential use with (b) BEZ235, or a pharmaceutically acceptable salt thereof, in the promotion and/or enhancement of an immune response in a subject.

BRIEF DESCRIPTION OF THE DRAWINGS

FIG. 5 shows that BEZ235 alone or in combination with RAD001 upregulate extracellular matrix remodeling proteins.

DETAILED DESCRIPTION OF CERTAIN EMBODIMENTS OF THE INVENTION

Figure 1:
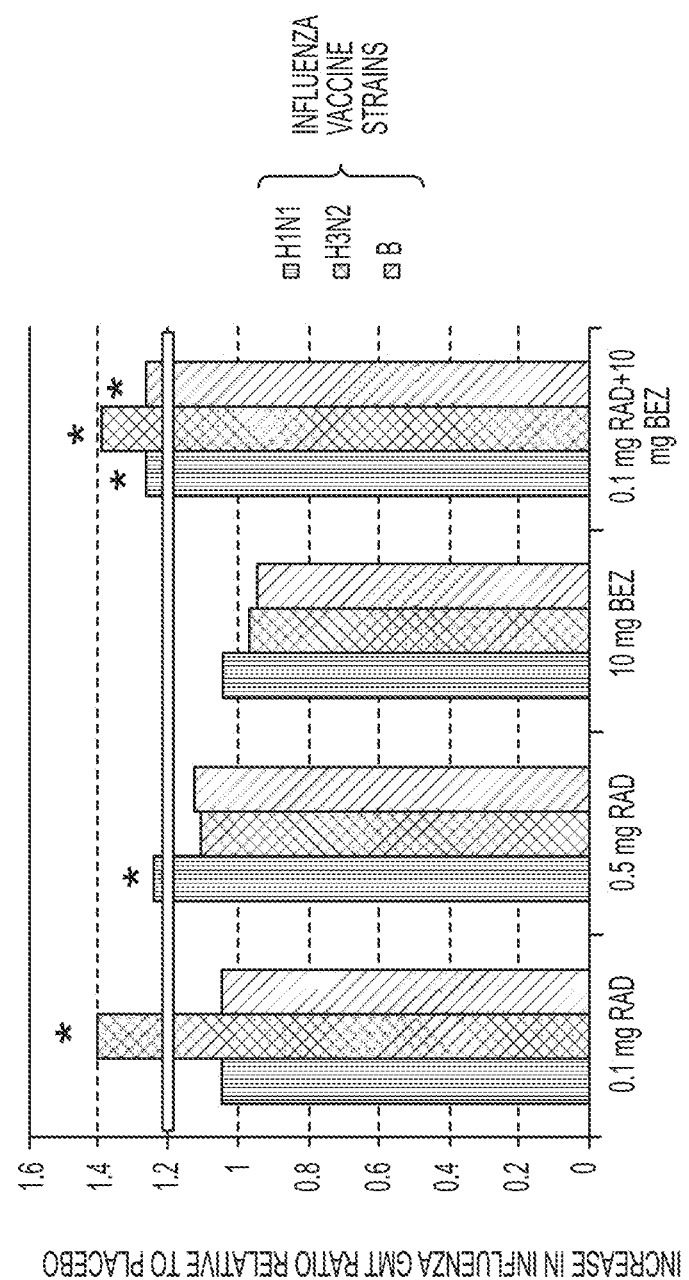
FIG. 1 shows the increase in antibody titers to influenza vaccine strains in RAD001 and/or BEZ235-treated versus placebo cohorts. Shown is the increase in the ratio (4 weeks after vaccination/baseline) in geometric mean titers (GMT) to each of the 3 influenza vaccine strains (A/H1N1 [A/California/7/2009], A/H3N2 [A/Texas/50/2012], or B [B/Massachusetts/2/2012]) in RAD001 and/or BEZ235-treated cohorts relative to the placebo cohort. The black bold line indicates the 1.2 fold increase in GMT ratios relative to placebo that is required in 2 out of 3 influenza vaccine strains in order to meet the primary endpoint of the study. Asterisks indicate that the probability that the increase in GMT relative to placebo exceeds 1.0 is 100%.

In one aspect, the present invention relates to (a) RAD001, or a pharmaceutically acceptable salt thereof; (b) BEZ235, or a pharmaceutically acceptable salt thereof; or (c) a combination thereof. In another aspect, the present invention provides a method of promoting and/or enhancing an immune response in a subject, comprising administering to the subject an effective amount of (a) RAD001, or a pharmaceutically acceptable salt thereof (b) BEZ235, or a pharmaceutically acceptable salt thereof; or (c) a combination thereof by simultaneous, separate or sequential administration.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" is defined herein to refer to either a fixed combination in one dosage unit form, a non-fixed combination or a kit of parts for the combined administration where RAD001, or pharmaceutically acceptable salt thereof, and BEZ235, or pharmaceutically acceptable salt thereof may be administered independently at the same time or separately within time intervals that allow that the combination partners show a cooperative, e.g., synergistic, effect.

The term "fixed combination" means that the active ingredients or therapeutic agents, e.g. RAD001 and BEZ235, are administered to a patient simultaneously in the form of a single entity or dosage form.

The term "non-fixed combination" means that the active ingredients or therapeutic agents, e.g. RAD001 and BEZ235, are both administered to a patient as separate entities or dosage forms either simultaneously, concurrently or sequentially with no specific time limits, wherein such administration provides therapeutically effective levels of the two compounds in the body of the subject, e.g., a mammal or human, in need thereof.

The term "pharmaceutical composition" is defined herein to refer to a mixture or solution containing at least one therapeutic agent to be administered to a subject, e.g., a mammal or human, in order to treat a particular disease or condition affecting the subject thereof.

The term "pharmaceutically acceptable" is defined herein to refer to those compounds, biologic agents, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The terms "combined administration" as used herein are defined to encompass the administration of the selected therapeutic agents to a single subject, e.g., a mammal or human, and are intended to include treatment regimens in which the agents are not necessarily administered by the same route of administration or at the same time.

The term "treating" or "treatment" as used herein comprises a treatment relieving, reducing or alleviating at least one symptom in a subject or affecting a delay of progression of a disease, condition and/or disorder. For example, treatment can be the diminishment of one or several symptoms of a disorder or complete eradication of a disorder. Within the meaning of the present invention, the term "treat" also denotes to arrest, delay the onset (i.e., the period prior to clinical manifestation of a disease) and/or reduce the risk of developing or worsening a disease.

The term "jointly therapeutically active" or "joint therapeutic effect" as used herein means that the therapeutic agents may be given separately (in a chronologically staggered manner, for example in a sequence-specific manner) such that the warm-blooded animal (for example, human) to be treated, still shows a interaction, such as a synergistic interaction (joint therapeutic effect). Whether this is the case can, inter alia, be determined by following the blood levels, showing that both therapeutic agents are present in the blood of the human to be treated at least during certain time intervals.

An "effective amount", "pharmaceutically effective amount", or "therapeutically effective amount" of a therapeutic agent is an amount sufficient to provide an observable improvement over the baseline clinically observable signs and symptoms of the promotion and/or enhancement of the immune response.

The term "synergistic effect" as used herein refers to action of two agents such as, for example, (a) RAD001, or a pharmaceutically acceptable salt thereof, and (b) BEZ235, or a pharmaceutically acceptable salt thereof, producing an effect, for example, promoting and/or enhancing an immune response in a subject, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The term "subject" or "patient" as used herein includes animals, which are capable of promoting and/or enhancing an immune response and/or having an age-related condition. Examples of subjects include mammals, e.g., humans, dogs, cows, horses, pigs, sheep, goats, cats, mice, rabbits, rats and transgenic non-human animals. In some embodiments, the subject is a human, e.g., a human suffering from, at risk of suffering from, or potentially capable of suffering from an age-related condition.

The term "about" or "approximately" shall have the meaning of within 10%, for example within 5%, of a given value or range.

The term "promote" or "enhance" in the context of an immune response refers to an increase in immune response, such as an increase in the ability of immune cells to target and/or kill cancer cells, to target and/or kill pathogens and pathogen infected cells, and protective immunity following vaccination, among others. In some embodiments, protective immunity refers to the presence of sufficient immune response (such as antibody titers) to protect against subsequent infection by a pathogen expressing the same antigen or protection against a new pathogen.

The terms "immunosenescence" or "immunosenescent" refer to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria.

Immunosenescence is a multifactorial condition leading to many pathologically significant health problems, e.g., in the aged population. Age-dependent biological changes such as a decline in function of hematopoietic stem cells, an increase in PD1+ lymphocytes, a decline in the function of phagocytes, macrophages, dendritic cells, monocytes, T cells, B cells and NK cells, and a decline in innate, cell-mediated or humoral immunity contribute to the onset of immunosenescence. In one aspect, immunosenescence can be measured in an individual by measuring telomere length in immune cells (See, e.g., U.S. Pat. No. 5,741,677). Immunosenescence can also be determined by documenting in an individual a lower than normal number of naïve CD4 and/or CD8 T cells, a decrease in early pro-B cells and pre-B cells, a decrease in T and B cell repertoire, an increase in the number of PD1-expressing T cells, e.g., a lower than normal number of PD-1 negative T cells, an increase in CD8+ CD28neg T cells, an increase in CD57+ and/or KLRG1+ CD8+ T cells, an increase in the number of LAG-3-positive T cells, a change in T cell surface glycoproteins, a change in antibody glycosylation, a change the glycosylation of proteins expressed intracellularly or on the surface of immune cells, an increase in ICOS, CTLA-4, Tim-3 and/or LAG-3 expressing CD4 T cells, or decreased response to vaccination in a subjects they age.

The term "impaired immune response" refers to a state in which a subject does not have an appropriate immune response, e.g., to cancer, vaccination, pathogen infection, among others. In some embodiments, a subject having an impaired immune response is predicted not to get protective antibody titer levels following prophylactic vaccination, or in which a subject does not have a decrease in cell-mediated immunity or disease burden after therapeutic vaccination. A subject can also have an impaired immune response if the subject has an impaired expression of innate immune response genes. A subject can also have an impaired immune response if the subject is a member of a population known to have decreased immune function or that has a history of decreased immune function such as the elderly, subjects undergoing chemotherapy treatment, asplenic subjects, immunocompromised subjects, or subjects having HIV/AIDS. Methods described herein allow for the treatment of an impaired immune response by administration of a low, immune enhancing, dose of an mTOR inhibitor, e.g., an allosteric mTOR inhibitor, such as RAD001.

The term "low, immune enhancing dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing dose of mTOR inhibitor results in a decrease in the number or percentage of PD-1 positive T cells and/or an increase in the number or percentage of PD-1 negative T cells, or an increase in the ratio of PD-1 negative T cells/PD-1 positive T cells. In an embodiment, the low, immune enhancing dose of mTOR inhibitor results in an increase in the number of naive T cells. In an embodiment, the low, immune enhancing dose of mTOR inhibitor results in one or more of the following:

an increase in the expression of interferon-induced genes in blood cells a decrease in the percentage of T cells expressing the markers LAG-3, CTLA-4, ICOS or Tim-3;

an increase in the expression of one or more of the following markers: CD62Lhigh, CD127high, CD27+, and BCL2, e.g., on memory T cells, e.g., memory T cell precursors;

a decrease in the expression of KLRG1 or CD57, e.g., on naïve or memory T cells, e.g., memory T cell precursors; and an increase in the number of memory T cell precursors, e.g., cells with any one or combination of the following characteristics: increased CD62Lhigh, increased CD127high, increased CD27+, decreased KLRG1, and increased BCL2;

wherein any of the changes described above occurs, e.g., at least transiently, e.g., as compared to a non-treated subject.

In an embodiment, a dose of an mTOR inhibitor is associated with, or provides, mTOR inhibition of at least 5 but no more than 90%, at least 10 but no more than 90%, at least 15 but no more than 90%, at least 20 but no more than 90%, at least 30 but no more than 90%, at least 40 but no more than 90%, at least 50 but no more than 90%, at least 60 but no more than 90%, or at least 70 but no more than 90%.

In an embodiment, a dose of an mTOR inhibitor is associated with, or provides, mTOR inhibition of at least 5 but no more than 80%, at least 10 but no more than 80%, at least 15 but no more than 80%, at least 20 but no more than 80%, at least 30 but no more than 80%, at least 40 but no more than 80%, at least 50 but no more than 80%, or at least 60 but no more than 80%.

In an embodiment, a dose of an mTOR inhibitor is associated with, or provides, mTOR inhibition of at least 5 but no more than 70%, at least 10 but no more than 70%, at least 15 but no more than 70%, at least 20 but no more than 70%, at least 30 but no more than 70%, at least 40 but no more than 70%, or at least 50 but no more than 70%.

In an embodiment, a dose of an mTOR inhibitor is associated with, or provides, mTOR inhibition of at least 5 but no more than 60%, at least 10 but no more than 60%, at least 15 but no more than 60%, at least 20 but no more than 60%, at least 30 but no more than 60%, or at least 40 but no more than 60%.

In an embodiment, a dose of an mTOR inhibitor is associated with, or provides, mTOR inhibition of at least 5 but no more than 50%, at least 10 but no more than 50%, at least 15 but no more than 50%, at least 20 but no more than 50%, at least 30 but no more than 50%, or at least 40 but no more than 50%.

In an embodiment, a dose of an mTOR inhibitor is associated with, or provides, mTOR inhibition of at least 5 but no more than 40%, at least 10 but no more than 40%, at least 15 but no more than 40%, at least 20 but no more than 40%, at least 30 but no more than 40%, or at least 35 but no more than 40%.

In an embodiment, a dose of an mTOR inhibitor is associated with, or provides, mTOR inhibition of at least 5 but no more than 30%, at least 10 but no more than 30%, at least 15 but no more than 30%, at least 20 but no more than 30%, or at least 25 but no more than 30%.

In an embodiment, a dose of an mTOR inhibitor is associated with, or provides, mTOR inhibition of at least 1, 2, 3, 4 or 5 but no more than 20%, at least 1, 2, 3, 4 or 5 but no more than 30%, at least 1, 2, 3, 4 or 5 but no more than 35, at least 1, 2, 3, 4 or 5 but no more than 40%, or at least 1, 2, 3, 4 or 5 but no more than 45%.

In an embodiment, a dose of an mTOR inhibitor is associated with, or provides, mTOR inhibition of at least 1, 2, 3, 4 or 5 but no more than 90%.

As is discussed herein, the extent of mTOR inhibition can be expressed as the extent of P70 S6K inhibition, e.g., the extent of mTOR inhibition can be determined by the level of decrease in P70 S6K activity, e.g., by the decrease in phosphorylation of a P70 S6K substrate. The level of mTOR inhibition can be evaluated by a method described herein, e.g. by the Boulay assay.

The term "promote" or "enhance" in the context of an immune response refers to an increase in immune response, such as an increase in the ability of immune cells to target and/or kill cancer cells, to target and/or kill pathogens and pathogen infected cells, and protective immunity following vaccination, among others. In some embodiments, protective immunity refers to the presence of sufficient immune response (such as antibody titers) to protect against subsequent infection by a pathogen expressing the same antigen.

mTOR Inhibitors

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

(A)

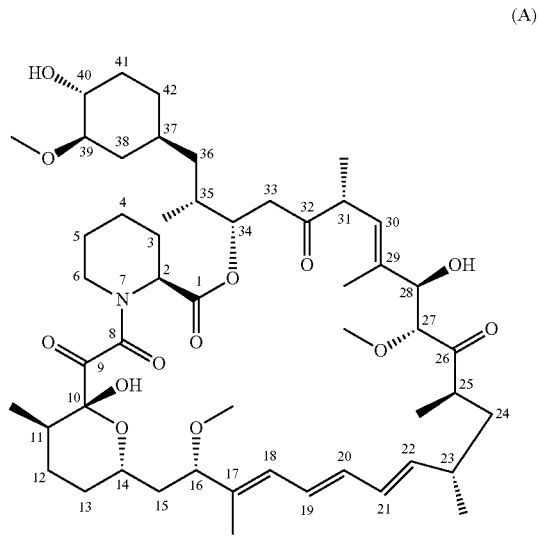 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by OR$_1$ in which R$_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolyl sulfonamidoethyl)-rapamycin, and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, for example (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807, the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin, and 32(S)-dihydro-40-O-(2-hydroxyethyl)-rapamycin.

Another suitable rapamycin analog is umirolimus as described in US 2005/0101624, the contents of which are incorporated by reference.

In mammalian cells, the target of rapamycin (mTOR) kinase exists as a multiprotein complex described as the mTORC1 complex or mTORC2 complex, which senses the availability of nutrients and energy and integrates inputs from growth factors and stress signalling. The mTORC1 complex is sensitive to allosteric mTOR inhibitors such as rapamycin, is composed of mTOR, GβL, and regulatory associated proteins of mTOR (raptor), and binds to the peptidyl-prolyl isomerase FKBP12 protein (a FK506-binding protein 1A, 12 kDa). In contrast, the mTORC2 complex is composed of mTOR, GβL, and rapamycin-insensitive companion proteins of mTOR (rictor), and does not bind to the FKBP12 protein in vitro.

The mTORC1 complex has been shown to be involved in protein translational control, operating as a growth factor and nutrient sensitive apparatus for growth and proliferation regulation. mTORC1 regulates protein translation via two key downstream substrates: P70 S6 kinase, which in turn phosphorylates ribosomal protein P70 S6, and eukaryotic translation initiation factor 4E binding protein 1 (4EBP1), which plays a key role in modulating eIF4E regulated cap-dependent translation. The mTORC1 complex regulates cell growth in response to the energy and nutrient homeostasis of the cell, and the deregulation of mTORC1 is common in a wide variety of human cancers. The function of mTORC2 involves the regulation of cell survival via phosphorylation of Akt and the modulation of actin cytoskeleton dynamics.

The mTORC1 complex is sensitive to allosteric mTOR inhibitors such as rapamycin and derivatives in large part due to rapamycin's mode of action, which involves the formation of an intracellular complex with the FKBP12 and binding to the FKBP12-rapamycin binding (FRB) domain of mTOR. This results in a conformational change in mTORC1 which is believed to alter and weaken the interaction with its scaffolding protein raptor, in turn impeding substrates such as P70 S6K1 from accessing mTOR and being phosphorylated. Rapamycin and rapalogues such as RAD001 have gained clinical relevance by inhibiting hyperactivation of mTOR associated with both benign and malignant proliferation disorders.

RAD001, otherwise known as everolimus (Afinitor®), has the chemical name (1R,9S,12S,15R,16E,18R,19R,21R, 23 S,24E,26E,28E,30S,32S,35R)-1,18-dihydroxy-12-{(1R)-2-[(1 S,3R,4R)-4-(2-hydroxyethoxy)-3-methoxycyclohexyl]-1-methylethyl}-19,30-dimethoxy-15,17,21,23,29, 35-hexamethyl-11,36-dioxa-4-aza-tricyclo[30.3.1.04,9] hexatriaconta-16,24,26,28-tetraene-2,3,10,14,20-pentaone and the following chemical structure

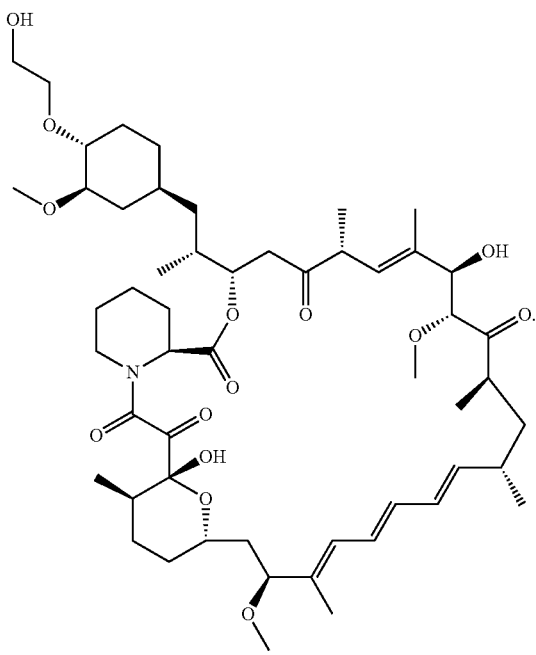 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

Everolimus is an FDA approved drug for the treatment of advanced kidney cancer and is being investigated in several other phase III clinical trials in oncology. Preclinical studies have shown that Everolimus is able to inhibit the proliferation of a wide variety of tumor cell lines both in vitro and in vivo, presumably through the suppression of rapamycin sensitive mTORC1 function. Everolimus, as a derivative of rapamycin, is an allosteric mTOR inhibitor that is highly potent at inhibiting part of the mTORC1 function, namely P70 S6 kinase (P70 S6K) and the downstream P70 S6K substrate P70 S6. Allosteric mTOR inhibitors like everolimus (and other rapamycin analogs) have little or no effect at inhibiting the mTORC2 pathway, or its resulting activation of Akt signalling. Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTOR inhibitors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more complete inhibitors of mTORC1 than such allosteric mTOR inhibitors as rapamycin, because they modulate rapamycin-resistant mTORC1 outputs such as 4EBP1-T37/46 phosphorylation and cap-dependent translation.

BEZ235 is a catalytic mTOR inhibitor, having the chemical name 2-methyl-2-[4-(3-methyl-2-oxo-8-quinolin-3-yl-2,3-dihydro-imidazo[4,5-c]quinolin-1-yl)-phenyl]-propionitrile and the following chemical structure

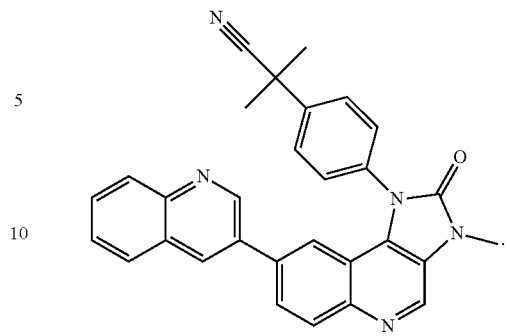

BEZ235 may also be used in its monotosylate salt form. The synthesis of BEZ235 is described in WO2006/122806, the contents of which are hereby incorporated by reference.

As a catalytic mTOR inhibitor, BEZ235 is capable of shutting down the complete function of mTORC1 complex, including both the rapamycin sensitive (phosphorylation of P70 S6K, and subsequently phosphorylation of P70 S6) and rapamycin insensitive (phosphorylation of 4EBP1) functions. BEZ235 has a differential effect according to the drug concentration used, whereby mTORC1 inhibition predominates at a very low concentration (less than or equal to 10 nmol/L), mTORC1 and mTORC2 inhibition predominates at low concentration (less than 200 nmol/L) but dual PI3K/mTOR inhibition at relatively higher concentrations (approximately 500 nmol/L).

The structure of the active ingredients identified by code numbers, generic or trade names may be taken from the actual edition of the standard compendium "The Merck Index" or from databases, e.g., Patents International (e.g., IMS World Publications). The corresponding content thereof is hereby incorporated by reference.

In some embodiments, the invention provides a combination comprising (a) RAD001 or a pharmaceutically acceptable salt thereof, and (b) BEZ235 or a pharmaceutically acceptable salt thereof, for simultaneous, separate or sequential use for the enhancement or promotion of an immune response in a subject.

In some embodiments, RAD001 is in the neutral form. In some embodiments, BEZ235 is the monotosylate salt. In some embodiments, RAD001 is administered in a dosage range from 0.01-0.2 mg, e.g. 0.1 mg. In some embodiments, BEZ235 is administered in a dosage range from 1-20 mg, e.g. 10 mg.

In some embodiments, the compound(s) or combination thereof is in an immediate release dosage form. In some embodiments, the compound(s) or combination thereof is administered once per week. In some embodiments, the compound(s) or combination thereof is administered once per day.

In some embodiments, the subject is immunocompromised. In some embodiments, the subject is HIV+ or has AIDS. In some embodiments, the subject has an infectious disease.

In some embodiments, the subject has an impaired immune response. In some embodiments, the subject is immunosenescent. In some embodiments, the subject has an age-related condition, e.g. immunosenescence.

In one embodiment of the invention, the invention provides a pharmaceutical composition comprising (a) RAD001, or a pharmaceutically acceptable salt thereof; (b)

BEZ235, or a pharmaceutically acceptable salt thereof or (c) a combination thereof and at least one pharmaceutically acceptable carrier.

Methods of Treatment

In one aspect, the present invention provides a method comprising the step of administering (a) a low dose of RAD001 or a pharmaceutically acceptable salt thereof; (b) a low dose of BEZ235 or a pharmaceutically acceptable salt thereof; or (c) a combination thereof, to a patient, wherein the patient experiences fewer illnesses due to infection than a patient not administered RAD001 or a pharmaceutically acceptable salt thereof, BEZ235 or a pharmaceutically acceptable salt thereof, or a combination thereof.

In some embodiments, the patient's innate immunity is enhanced.

In some embodiments, antigen-specific immunity is not enhanced.

In some embodiments, at least one interferon-inducing gene (ISG) is upregulated.

In some embodiments, the infection is a urinary tract infection.

In some embodiments, the infection is an infection of the teeth or gums.

In some embodiments, the infection is a respiratory tract infection.

In some embodiments, the infection is a viral infection.

In some embodiments, the patient is elderly.

In some embodiments, the patient is at least 65 years old.

In some embodiments, the patient is at least 75 years old.

In some embodiments, the patient is at least 85 years old.

In some embodiments, the low dose of RAD001 or a pharmaceutically acceptable salt thereof, the low dose of BEZ235 or a pharmaceutically acceptable salt thereof, or combination thereof, is administered to the patient for up to about 6 consecutive weeks; up to about 8 consecutive weeks; up to about 10 consecutive weeks; up to about 12 consecutive weeks; up to about 16 consecutive weeks; up to about 20 consecutive weeks; up to about 6 consecutive months; up to about 1 year; or as part of long-term treatment (indefinitely).

In some embodiments, the low dose of BEZ235 or a pharmaceutically acceptable salt thereof is administered to the patient for up to about 3 consecutive weeks; up to about 6 consecutive weeks; up to about 8 consecutive weeks; up to about 10 consecutive weeks; up to about 12 consecutive weeks; up to about 16 consecutive weeks; up to about 20 consecutive weeks; up to about 24 consecutive weeks; or up to about 6 consecutive months.

In some embodiments, the patient continues to experience fewer illnesses due to infection from about 1 day until about 1 year after the administration of the RAD001 or a pharmaceutically acceptable salt thereof, the BEZ235 or a pharmaceutically acceptable salt thereof, or combination thereof.

In some embodiments, the patient continues to experience fewer illnesses due to infection for at least 1 month and until about 1 year after the administration of the RAD001 or a pharmaceutically acceptable salt thereof, the BEZ235 or a pharmaceutically acceptable salt thereof, or combination thereof.

In some embodiments, the patient continues to experience fewer illnesses due to infection for at least 3 months and until about 1 year after the administration of the RAD001 or a pharmaceutically acceptable salt thereof, the BEZ235 or a pharmaceutically acceptable salt thereof, or combination thereof.

In some embodiments, the patient continues to experience fewer illnesses due to infection for at least 6 months after the administration of the RAD001 or a pharmaceutically acceptable salt thereof, the BEZ235 or a pharmaceutically acceptable salt thereof, or combination thereof.

In some embodiments, the patient is administered the low dose of BEZ235 or a pharmaceutically acceptable salt thereof as a monotherapy.

In some embodiments, the patient is administered the low dose of RAD001 or a pharmaceutically acceptable salt thereof as a monotherapy.

In some embodiments, the patient is administered both the low dose of RAD001 or a pharmaceutically acceptable salt thereof and the low dose of BEZ235 or a pharmaceutically acceptable salt thereof as a combination therapy.

In some embodiments, the pharmacokinetic AUC variability of patients receiving the low dose of BEZ235 or a pharmaceutically acceptable salt thereof is lower than a patient receiving a higher dose of BEZ235 or a pharmaceutically acceptable salt thereof.

In some embodiments, RAD001 or a pharmaceutically acceptable salt thereof is in the neutral form.

In some embodiments, BEZ235 or a pharmaceutically acceptable salt thereof is the monotosylate salt.

In some embodiments, the method comprises the administration of 0.01-0.2 mg of RAD001 or a pharmaceutically acceptable salt thereof.

In some embodiments, the method comprises the administration of 1-50 mg of BEZ235 or a pharmaceutically acceptable salt thereof.

In some embodiments, the subject is immunocompromised.

In some embodiments, the subject has an impaired immune response.

In some embodiments, the subject is immunosenescent.

In one aspect, the present invention provides a method of upregulating at least one interferon-inducing gene (ISG), comprising administering (a) a low dose of RAD001 or a pharmaceutically acceptable salt thereof; (b) a low dose of BEZ235 or a pharmaceutically acceptable salt thereof; or (c) a combination thereof, to a patient.

In one aspect, the present invention provides a method of upregulating at least one protein involved in extracellular matrix remodeling, comprising administering (a) a low dose of RAD001 or a pharmaceutically acceptable salt thereof; (b) a low dose of BEZ235 or a pharmaceutically acceptable salt thereof; or (c) a combination thereof, to a patient.

In some embodiments, the protein involved in extracellular matrix remodeling is significantly upregulated following treatment for at least 1 day, about 1 week, about 3 weeks, about 4 weeks, about 5 weeks, about 6 weeks, about 8 weeks, about 10 weeks, about 12 weeks, about 16 weeks, about 20 weeks, about 24 weeks, or about 6 months.

In some embodiments, the present invention provides a method of treating a disease or condition associated with aberrant extracellular matrix remodeling, comprising administering (a) a low dose of RAD001 or a pharmaceutically acceptable salt thereof; (b) a low dose of BEZ235 or a pharmaceutically acceptable salt thereof; or (c) a combination thereof, to a patient.

In some embodiments, the disease or condition associated with aberrant extracellular matrix remodeling is selected from heart failure, such as heart failure with preserved ejection fraction, chronic renal failure, glomerunephropathy, skin aging, NASH, hepatitis fibrosis/cirrhosis, pulmonary fibrosis including idiopathic pulmonary fibrosis, aging-related tendon dysfunction/stiffening, arthritis including osteoarthritis, sarcopenia, myelofibrosis, myelodysplasia, aging-related dysfunction of the blood brain barrier, diabetic nephropathy, atherosclerosis, or wound healing.

In some embodiments, the invention provides a method of promoting or enhancing an immune response in a subject comprising administering to said subject (a) RAD001, or a pharmaceutically acceptable salt thereof; (b) BEZ235, or a pharmaceutically acceptable salt thereof; or (c) a combination thereof in an amount which is therapeutically effective or jointly therapeutically effective at promoting or enhancing an immune response.

In some embodiments, the invention provides a method of treating an age-related condition in a subject comprising administering to said subject (a) RAD001, or a pharmaceutically acceptable salt thereof; (b) BEZ235, or a pharmaceutically acceptable salt thereof; or (c) a combination thereof in a quantity which is therapeutically effective or jointly therapeutically effective to treat, prevent, or ameliorate an age-related condition, e.g. immunosenescence.

In some embodiments, the invention provides the use of (a) RAD001, or a pharmaceutically acceptable salt thereof; (b) BEZ235, or a pharmaceutically acceptable salt thereof; or (c) a combination thereof for the preparation of a medicament for the promotion or enhancement of an immune response.

In some embodiments, the invention provides the use of (a) RAD001, or a pharmaceutically acceptable salt thereof; (b) BEZ235, or a pharmaceutically acceptable salt thereof; or (c) a combination thereof for the preparation of a medicament for the treatment of an age-related condition, e.g. immunosenescence.

In some embodiments, the invention provides a commercial package comprising RAD001, or a pharmaceutically acceptable salt thereof, and instructions for the simultaneous, separate or sequential use with BEZ235, or a pharmaceutically acceptable salt thereof, in the promotion or enhancement of an immune response.

In some embodiments, the invention provides a commercial package comprising RAD001, or a pharmaceutically acceptable salt thereof, and instructions for the simultaneous, separate or sequential use with BEZ235, or a pharmaceutically acceptable salt thereof, in the treatment of an age-related condition.

In some embodiments, a benefit of the use of the combination is that lower doses of (a) RAD001, or a pharmaceutically acceptable salt thereof and (b) BEZ235, or a pharmaceutically acceptable salt thereof, when used in combination can be used, for example, that the dosages need not only often be smaller, but are also applied less frequently, or exhibit diminished incidence of side-effects observed with larger doses or with one of the combination partners alone. This is in accordance with the desires and requirements of the patients to be treated.

It can be shown by established test models that administration of (a) RAD001, or a pharmaceutically acceptable salt thereof; (b) BEZ235, or a pharmaceutically acceptable salt thereof; or (c) a combination thereof results in the beneficial effects described herein before. The person skilled in the art is fully enabled to select a relevant test model to prove such beneficial effects. The pharmacological activity of a compound or combination may, for example, be demonstrated in a clinical study or in an in vivo or in vitro test procedure as known in the art or as described hereinafter.

In one aspect, the invention provides a pharmaceutical composition comprising a quantity, which is jointly therapeutically effective at promoting and/or enhancing an immune response in a subject, of (a) RAD001, or a pharmaceutically acceptable salt thereof; and (b) BEZ235, or a pharmaceutically acceptable salt thereof. In this composition, the combination partners (a) and (b) are administered in a single formulation or unit dosage form by any suitable route. The unit dosage form may also be a fixed combination.

In a further aspect, the invention provides pharmaceutical compositions separately comprising a quantity, which is jointly therapeutically effective at promoting and/or enhancing an immune response in a subject, of (a) RAD001, or a pharmaceutically acceptable salt thereof and (b) BEZ235, or a pharmaceutically acceptable salt thereof which are administered concurrently but separately, or administered sequentially.

The pharmaceutical compositions for separate administration of the combination partners, or for the administration in a fixed combination, i.e. a single galenical composition comprising (a) RAD001, or a pharmaceutically acceptable salt thereof; and (b) BEZ235, or a pharmaceutically acceptable salt thereof, may be prepared in a manner known in the art and are those suitable for enteral (such as oral or rectal) and/or parenteral administration to subjects and comprising a therapeutically effective amount of at least one combination partner alone, e.g. as indicated above, or in combination with one or more pharmaceutically acceptable carriers.

The novel pharmaceutical composition may contain from about 0.1% to about 99.9%, for example from about 1% to about 60%, of the active ingredient(s).

In some embodiments according to any of the preceding embodiments, the subject is at least 65 years of age.

In some embodiments, the subject has congestive heart failure,

In some embodiments, the subject has diabetes mellitus.

In some embodiments, the subject has chronic renal failure.

In some embodiments, the subject is a current smoker.

In some embodiments, the subject has COPD.

Chronic obstructive pulmonary disease (COPD) is a lung disease characterized by chronic obstruction of lung airflow that interferes with normal breathing and is not fully reversible. The more familiar terms "chronic bronchitis" and "emphysema" are no longer used, but are now included within the COPD diagnosis. COPD is not simply a "smoker's cough" but an under-diagnosed, life-threatening lung disease. A COPD diagnosis is confirmed by a simple test called spirometry, which measures how deeply a person can breathe and how fast air can move into and out of the lungs. Such a diagnosis should be considered in any patient who has symptoms of cough, sputum production, or dyspnea (difficult or labored breathing), and/or a history of exposure to risk factors for the disease. Where spirometry is unavailable, the diagnosis of COPD should be made using all available tools. Clinical symptoms and signs, such as abnormal shortness of breath and increased forced expiratory time, can be used to help with the diagnosis. A low peak flow is consistent with COPD, but may not be specific to COPD because it can be caused by other lung diseases and by poor performance during testing. Chronic cough and sputum production often precede the development of airflow limitation by many years, although not all individuals with cough and sputum production go on to develop COPD.

In some embodiments, the subject resides in a nursing home facility.

In some embodiments, the subject is residing in an assisted living facility.

In some embodiments, the subject resides in a skilled nursing facility.

In some embodiments, the subject resides in a rehabilitation facility.

In some embodiments, the subject requires assistance with one or more activity of daily living.

Activities of daily living (ADL) are routine activities that people tend do every day without needing assistance. There are six basic ADLs: eating, bathing, dressing, toileting, transferring (walking) and continence. An individual's ability to perform ADLs is important for determining what type of long-term care (e.g. nursing-home care or home care) and coverage the individual needs (i.e. Medicare, Medicaid or long-term care insurance).

ADLs (activities of daily living): the things we normally do in daily living including any daily activity we perform for self-care such as cooking, feeding, bathing, dressing, grooming, work, homemaking, and leisure. The ability or inability to perform ADLs can be used as a very practical measure of ability/disability in many disorders.

In some embodiments, the subject has mobility disability.

Mobility disability or mobility impairment refers to the impaired ability of a person to use one or more of his/her extremities, or a decrease in strength needed to walk, grasp, or lift objects. The use of a wheelchair, crutches, or a walker may be utilized to aid in mobility. Mobility impairment may be caused by a number of factors, such as aging-related sarcopenia, disease, an accident, or a congenital disorder and may be the result from muscular, neuro-muscular or orthopaedic impairments.

Pharmaceutical compositions comprising a disclosed compound or combination, including fixed combinations or non-fixed combinations, for enteral or parenteral administration are, for example, those in unit dosage forms, such as sugar-coated tablets, tablets, capsules or suppositories, or ampoules. If not indicated otherwise, these are prepared in a manner known in the art, for example by means of various conventional mixing, comminution, granulating, sugar-coating, dissolving, lyophilizing processes, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units. It will be further appreciated that the unit content of a combination partner for parenteral administration may contain a higher dosage amount of the combination partner which is diluted to the effective dosage amount before administration.

A unit dosage form containing the combination of agents or individual agents of the combination of agents may be in the form of micro-tablets enclosed inside a capsule, e.g. a gelatin capsule. For this, a gelatin capsule as is employed in pharmaceutical formulations can be used, such as the hard gelatin capsule known as CAPSUGEL®, available from Pfizer.

The unit dosage forms of the present invention may optionally further comprise additional conventional carriers or excipients used for pharmaceuticals. Examples of such carriers include, but are not limited to, disintegrants, binders, lubricants, glidants, stabilizers, and fillers, diluents, colorants, flavors, and preservatives. One of ordinary skill in the art may select one or more of the aforementioned carriers with respect to the particular desired properties of the dosage form by routine experimentation and without any undue burden. The amount of each carrier used may vary within ranges conventional in the art. The following references which are all hereby incorporated by reference disclose techniques and excipients used to formulate oral dosage forms. See *The Handbook of Pharmaceutical Excipients,* 4th edition, Rowe et al., Eds., American Pharmaceuticals Association (2003); and Remington: the Science and Practice of Pharmacy, 20th edition, Gennaro, Ed., Lippincott Williams & Wilkins (2003).

These optional additional conventional carriers may be incorporated into the oral dosage form either by incorporating the one or more conventional carriers into the initial mixture before or during melt granulation or by combining the one or more conventional carriers with the granules in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL™ from International Specialty Products (Wayne, N.J.); cross-linked sodium carboxymethylcellulose or croscarmellose sodium, e.g., AC-DI-SOL™ from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH™ from FMC (Philadelphia, Pa.), hydroxypropyl cellulose hydroxylethyl cellulose and hydroxylpropylmethyl cellulose METHOCEL™ from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

The optimum ratios, individual and combined dosages, and concentrations of the therapeutic agent or agents that yield efficacy without toxicity are based on the kinetics of the therapeutic agent's availability to target sites, and are determined using methods known to those of skill in the art.

In accordance with the present invention, a therapeutically effective amount of each of (a) RAD001, or a pharmaceutically acceptable salt thereof; (b) BEZ235, or a pharmaceutically acceptable salt thereof; or (c) a combination thereof may be administered simultaneously or sequentially and in any order, and the components may be administered separately or as a fixed combination. For example, in one aspect the invention provides a method of preventing or treating an infection or age-related disease according to the invention may comprise (i) administration of the first agent (a) in free or pharmaceutically acceptable salt form, and (ii) administration of an agent (b) in free or pharmaceutically acceptable salt form, simultaneously or sequentially in any order, in jointly therapeutically effective amounts, in some embodiments in synergistically effective amounts, e.g. in daily or intermittent dosages corresponding to the amounts described herein. The individual therapeutic agents may be administered separately at different times during the course of therapy or concurrently in divided or single combination forms. Furthermore, the term "administering" also encompasses the use of a pro-drug of a therapeutic agent that converts in vivo to the therapeutic agent. The instant invention is therefore to be understood as embracing all such regimens of simultaneous or alternating treatment and the term "administering" is to be interpreted accordingly.

The effective dosage of each of the therapeutic agents or combination thereof may vary depending on the particular therapeutic agent or pharmaceutical composition employed, the mode of administration, the condition being treated, and the severity of the condition being treated. Thus, the dosage regimen is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition.

In embodiments where two therapeutic agents are used in combination, the effective dosage of each of the therapeutic agents may require more frequent administration of one of the therapeutic agent(s) as compared to the other therapeutic agent(s) in the combination. Therefore, to permit appropriate dosing, packaged pharmaceutical products may contain one or more dosage forms that contain the combination of compounds, and one or more dosage forms that contain one of the combination of therapeutic agent(s), but not the other therapeutic agent(s) of the combination.

When the combination of therapeutic agents, such as a combination of (a) RAD001, or a pharmaceutically acceptable salt thereof; and (b) BEZ235, or a pharmaceutically acceptable salt thereof are applied in the form as marketed as single drugs, their dosage and mode of administration can be in accordance with the information provided on the package insert of the respective marketed drug, if not mentioned herein otherwise.

In some embodiments, RAD001, for example its free form, is administered orally at a dose in the range from about 0.01 mg to about 1 mg daily and/or weekly. In some embodiments, the dosage of RAD001, particularly its free form, is administered orally at a dosage of 0.1 mg daily to an adult person.

In some embodiments, BEZ235 or a pharmaceutically acceptable salt thereof, for example its p-toluenesulfonate salt, is administered orally at a dose in the range from about 1 mg to about 20 mg daily or about 1 mg to about 50 mg daily and/or weekly. In some embodiments, the dosage of BEZ235 or a pharmaceutically acceptable salt thereof, such as its p-toluenesulfonate salt, is administered, for example orally, at a dosage of about 10 mg daily to an adult person, such as a person aged 65 years or older. In some embodiments, the dosage of BEZ235 or a pharmaceutically acceptable salt thereof is from about 2 mg to about 19 mg, about 3 mg to about 17 mg, about 4 mg to about 16 mg, about 5 mg to about 15 mg, about 6 mg to about 14 mg, about 7 mg to about 13 mg, about 8 mg to about 12 mg, or about 9 mg to about 11 mg. In some embodiments, the dose of BEZ235 or a pharmaceutically acceptable salt thereof is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg, or about 50 mg. In some embodiments, BEZ235 is administered orally as its p-toluenesulfonate salt. In some embodiments, BEZ235 or a pharmaceutically acceptable salt thereof is administered twice per day, once per day, once every two days, once every three days, once every four days, once every five days, once every six days, once a week, once every two weeks, once every three weeks, once every four weeks, once a month, once every two months, once every three months, once every four months, once every six months, or once per year.

The optimal dosage of each therapeutic agent for promotion and/or enhancement of an immune response in a subject and/or treating an age-related condition in a subject can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each therapeutic agent that may be combined with the carrier materials to produce a single dosage form will vary depending upon the individual treated and the particular mode of administration. In some embodiments the unit dosage forms containing the combination of therapeutic agents as described herein will contain the amounts of each agent of the combination that are typically administered when the therapeutic agents are administered alone.

Frequency of dosage may vary depending on the therapeutic agent used and the particular condition to be treated. In general, the use of the minimum dosage that is sufficient to provide effective therapy is preferred. Patients may generally be monitored for therapeutic effectiveness using assays suitable for the condition being treated, which will be familiar to those of ordinary skill in the art.

In one aspect, the present invention provides a method of promoting and/or enhancing an immune response in a subject comprising administering to subject in need thereof (a) RAD001, or a pharmaceutically acceptable salt thereof; (b) BEZ235, or a pharmaceutically acceptable salt thereof; or (c) a combination thereof in an amount which is therapeutically effective or jointly therapeutically effective at promoting and/or enhancing an immune response in a subject.

In another aspect, the present invention provides a method of treating an age-related condition in a subject, comprising administering to a subject in need thereof an amount of (a) RAD001, or a pharmaceutically acceptable salt thereof; (b) BEZ235, or a pharmaceutically acceptable salt thereof; or (c) a combination thereof in an amount which is therapeutically effective or jointly therapeutically effective to treat an age-related condition, such as immunosenescence.

In another aspect, the present invention provides a method of promoting and/or enhancing an immune response in a subject comprising administering to subject in need thereof. BEZ235, or a pharmaceutically acceptable salt thereof in an amount which is therapeutically effective at promoting and/or enhancing an immune response in a subject, such as an innate immune response.

In another aspect, the present invention provides a method of treating an age-related condition in a subject, comprising administering to a subject in need thereof an amount of BEZ235, or a pharmaceutically acceptable salt thereof in an amount which is therapeutically effective to treat an age-related condition, such as immunosenescence.

In another aspect, the present invention provides the use of (a) RAD001, or a pharmaceutically acceptable salt thereof; (b) BEZ235, or a pharmaceutically acceptable salt thereof; or (c) a combination thereof for the enhancement and/or promotion of an immune response and/or for the preparation of a medicament for the enhancement and/or promotion of an immune response.

In another aspect, the present invention provides the use of (a) RAD001, or a pharmaceutically acceptable salt thereof; (b) BEZ235, or a pharmaceutically acceptable salt thereof; or (c) a combination thereof for the treatment of an age-related condition and/or for the preparation of a medicament for the treatment of an age-related condition, such as immunosenescence.

In another aspect, the present invention provides the use of BEZ235, or a pharmaceutically acceptable salt thereof for the enhancement and/or promotion of an immune response and/or for the preparation of a medicament for the enhancement and/or promotion of an immune response, such as an innate immune response.

In another aspect, the present invention provides the use of BEZ235, or a pharmaceutically acceptable salt thereof for the treatment of an age-related condition and/or for the preparation of a medicament for the treatment of an age-related condition, such as immunosenescence.

In one aspect, the present invention provides a commercial package comprising as active ingredients (a) RAD001, or a pharmaceutically acceptable salt thereof; (b) BEZ235, or a pharmaceutically acceptable salt thereof; or (c) a combination thereof together with instructions for the simultaneous, separate or sequential use thereof in the enhancement and/or treatment of an immune response.

In another aspect, the present invention provides a commercial package comprising as active ingredients (a) RAD001, or a pharmaceutically acceptable salt thereof; (b) BEZ235, or a pharmaceutically acceptable salt thereof; or (c) a combination thereof together with instructions for the simultaneous, separate or sequential use thereof in the treatment of an age-related condition, such as immunosenescence.

In one aspect, the present invention provides a commercial package comprising RAD001, or a pharmaceutically acceptable salt thereof, and instructions for the simultaneous, separate or sequential use with BEZ235 or a pharmaceutically acceptable salt thereof, in the enhancement and/or promotion of an immune response.

In another aspect, the present invention provides a commercial package comprising RAD001, or a pharmaceutically acceptable salt thereof, and instructions for the simultaneous, separate or sequential use with BEZ235 or a pharmaceutically acceptable salt thereof, in the treatment of an age-related condition, such as immunosenescence.

In another aspect, the present invention provides a commercial package comprising BEZ235, or a pharmaceutically acceptable salt thereof, and instructions for the simultaneous, separate or sequential use with RAD001 or a pharmaceutically acceptable salt thereof, in the enhancement and/or promotion of an immune response, such as an innate immune response.

In another aspect, the present invention provides a commercial package comprising BEZ235, or a pharmaceutically acceptable salt thereof, and instructions for the simultaneous, separate or sequential use with RAD001 or a pharmaceutically acceptable salt thereof, in the treatment of an age-related condition, such as immunosenescence.

In another aspect, the present invention provides a commercial package comprising BEZ235, or a pharmaceutically acceptable salt thereof, and instructions for use in the enhancement and/or promotion of an immune response, such as an innate immune response.

In another aspect, the present invention provides a commercial package comprising BEZ235, or a pharmaceutically acceptable salt thereof, and instructions for use in the treatment of an age-related condition, such as immunosenescence.

Pathogenic Infections

In another aspect, the methods provided herein can be used to treat or prevent an infection by a pathogen in a subject. In some embodiments, the subject is immunodeficient. In some embodiments, the subject is immunosenescent. In some embodiments, the pathogen is a viral pathogen, e.g., a viral pathogen e.g. HIV, meningitis causing viruses, encephalitis causing viruses, Hepatitis A, Hepatitis B, Hepatitis C, rabies virus, polio virus, influenza virus, parainfluenza virus, adenovirus, rhinovirus, measles virus, mumps virus, rubella, pertussis, papilloma virus, yellow fever virus, respiratory syncytial virus, parvovirus, Norwalk virus, chikungunya virus, hemorrhagic fever viruses including Ebola virus, dengue virus, Zika virus, and Herpes viruses, e.g., varicella, cytomegalovirus and Epstein-Barr virus. In some embodiments, the infection is a viral infection, such as a chronic viral infection. In some embodiments, a chronic viral infection is selected from Hepatitis A, Hepatitis B, Hepatitis C, Epstein-Barr Virus, HIV, Cytomegalovirus, Herpes Simplex Virus 1, Herpes Simplex Virus 2, Human Papillomavirus, Adenovirus, and Kaposi's Sarcoma-Associated Herpesvirus. In some embodiments, a chronic viral infection comprises HIV.

For example, Lichterfeld and colleagues observed that HIV-specific CD8+ T-cells showed reduced telomere length and an increase in telomere length and telomerase activity upon inhibition of PD-1 (see e.g., Lichterfeld, M et al. (2008) Blood 112(9):3679-3687). In another example, PD-1 was significantly upregulated in hepatitis C (HVC)-specific CD8+ cytotoxic T lymphocytes (see e.g., Golden-Mason, L (2007) J. Virol. 81(17): 9249-9258).

In some embodiments, a viral infection comprises a viral respiratory tract infection. In some embodiments, the viral respiratory tract infection is an upper viral respiratory tract infection. In some embodiments, the viral respiratory tract infection is a lower viral respiratory tract infection. In some embodiments, the viral respiratory tract infection is caused by a rhinovirus, coronavirus, influenza virus, respiratory syncytial virus (RSV), adenovirus, metapneumovirus, enterovirus, bocavirus paramyxovirus, and/or parainfluenza virus. In some embodiments, a viral respiratory tract infection is pneumonia. In some embodiments, a viral respiratory tract infection includes a lung abscess. In some embodiments, a viral respiratory tract infection includes bronchitis.

In some embodiments, the pathogen is a bacterial pathogen, e.g., a bacterial pathogen selected from *Meningococcus, Haemophilus, Pneumococcus, Staphylococcus, Streptococcus, Neisseria, Moraxella, Escherichia coli,*

*Klebsiella, Pseudomonas, Enterobacter, Proteus, Serratia, Legionella, Salmonella, Shigella, Acinetobacer, Listeria, Chlamydia,* and *Mycobacterium,* among others.

In some embodiments, the pathogen is a parasitic pathogen, e.g., *Toxoplasma, Leishmania* and malaria, *T. cruzii,* Helminth, e.g., *Schistosoma.*

In some embodiments, the pathogen is a yeast or fungal pathogen, e.g., *Candida, Cryptococcus, Coccidioides, Blastomyces, aspergillus,* or mucormycetes.

Senescence and Other Disorders

In another aspect, the methods provided herein can be used to treat senescence in a subject. As used herein, the term "senescence" is meant to include all types of aging. In some embodiments, senescence comprises immunodeficiency, for example immunosenescence. Immunosenescence includes reduced immune response to infection with age and results from thymic involution in T-cell lineages, resulting in decreased T cell production and export (see e.g., Shimatani, K et al. (2009) PNAS 106 (37):15807-15812). In some embodiments, there is an increase in population of a bona fide age-dependent CD4+ or CD8+ T cell population defined by a persistent expression of PD-1, which inhibits T cell responses to antigens (see e.g., Shimatani, K et al. (2009) PNAS 106 (37):15807-15812; Nunes, C et al. (2012) Clinical Cancer Research 18(3):678-687). In some embodiments, senescence comprises cellular senescence, in which a cell no longer divides. In some embodiments, age-related immunosenescence comprises decreased production of naive lymphocytes by hematopoietic stem cells (Chen, Science Signalling, ra75, 2009). Cellular senescence is correlated with the progressive shortening of telomeres that occurs with each cell division or the intracellular expression of p16. In some embodiments senescence comprises an age-related decrease in the function of neutrophils, lymphocytes, NK cells, macrophages and/or dendritic cells (see e.g. Boraschi D et al. (2013) Sci Transl Med 5(185):ps8; Kumar R and Burns E A. (2008) Expert Rev. Vaccines 7(4): 467-479.

EXEMPLIFICATION

The following Examples illustrate the invention described above; they are not, however, intended to limit the scope of the invention in any way. The beneficial effects of the pharmaceutical compounds, combinations, and compositions of the present invention can also be determined by other test models known as such to the person skilled in the pertinent art.

Example 1: Data Supporting a Claim that BEZ235 does not Enhance Antigen Specific Immunity but Decreases Infection Rates by Enhancing Innate Immunity Via Upregulation of Interferon-Induced Genes (ISGs)

A total of 264 elderly volunteers ≥65 years of age, without unstable medical conditions, were enrolled in a randomized double blind placebo-controlled trial. Subjects were randomly assigned to receive placebo or one of four oral mTOR inhibitor dosing regimens: RAD001: 0.5 mg daily, RAD001 0.1 mg daily, BEZ235 10 mg daily, or a combination of 0.1 mg RAD001 and 10 mg BEZ235 daily. Subjects were treated for 6 weeks with study drug and, after a 2 week drug-free interval, were given a 2014 seasonal influenza vaccine (Fluvax®, CSL Biotherapies). Hemagglutination inhibition (HI) antibody titers to the 3 strains of influenza in the influenza vaccine were measured in serum collected at baseline and four weeks after influenza vaccination. Serum HI titers were measured at Quest Diagnostics. The subjects were then followed for another 9 months off study drug. The primary endpoint of the study was a 1.2 fold increase relative to placebo in the hemagglutination inhibition (HI) geometric mean titer (GMT) ratio (GMT 4 weeks post vaccination/GMT at baseline) to at least 2 out of 3 influenza vaccine strains. This endpoint was chosen because an approximately 1.2-fold increase in the influenza GMT ratio induced by the MF-59 vaccine adjuvant was associated with a decrease in influenza illness (1).

Only the combination of low dose RAD001 (0.1 mg daily) and BEZ235 (10 mg daily) met the primary endpoint of the study and resulted in a statistically significant greater than 1.2-fold increase in the influenza GMT ratio in 3/3 influenza vaccine strains (FIG. 1). RAD001 monotherapy (0.1 mg or 0.5 mg daily) resulted in a statistically significant greater than 1.2-fold increase in influenza GMT ratio in only 1/3 influenza vaccine strains. BEZ235 monotherapy did not result in an increase in influenza GMT ratios to any of the 3 influenza vaccine strains. These results suggest that a combination of a low dose allosteric (RAD001) and catalytic (BEZ235) mTOR inhibitor resulted in greater improvement in influenza vaccination response than RAD001 or BEZ235 monotherapy.

As an additional assessment of immune function, the overall infection rate in each treatment group was assessed by having subjects record any infections they experienced during the year following the initiation of study drug treatment in a diary that was reviewed by study investigators at each study visit. The number of infections per person per year was significantly decreased relative to placebo in the subjects in the RAD001 0.1 mg+BEZ235 10 mg combination and in the BEZ235 monotherapy treatment groups (Table 1). In addition, the rate of urinary tract infections (Table 2) and tooth and gum infections (Table 3) were lower in the BEZ235 monotherapy and RAD001+BEZ235 treatment groups than in the placebo or RAD001 monotherapy treatment groups.

TABLE 1

BEZ235 alone or in combination with RAD001 was associated with a significant reduction in infection rates for one year after study drug administration Infection rate/person for one year after study drug administration

| RAD001 0.1 mg daily | RAD001 0.5 mg daily | BEZ235 10 mg daily | RAD001 0.1 mg and BEZ235 10 mg daily | Placebo |
|---|---|---|---|---|
| 2.0 | 2.1 | 1.8* | 1.7** | 2.5 |

*p = 0.015;
**p = 0.003

TABLE 2

BEZ235 alone or in combination with RAD001 was associated with a reduction in the percentage of subjects with urinary tract infections for one year after study drug administration Percent of subjects with urinary tract infections during one year after study drug administration

| RAD001 0.1 mg daily N = 51 | RAD001 0.5 mg daily N = 46 | BEZ235 10 mg daily N = 46 | RAD001 0.1 mg and BEZ235 10 mg daily N = 53 | Placebo N = 48 |
|---|---|---|---|---|
| 10 | 11 | 4 | 0 | 12 |

TABLE 3

BEZ235 alone or in combination with RAD001 was
associated with a reduction in the rate of tooth or gum
infections for one year after study drug administration
Number of tooth or gum infections per person for one
year after study drug administration

| RAD001 0.1 mg daily | RAD001 0.5 mg daily | BEZ235 10 mg daily | RAD001 0.1 mg and BEZ235 10 mg daily | Placebo |
|---|---|---|---|---|
| .02 | .02 | .02 | .04 | .13 |

Figure 2:
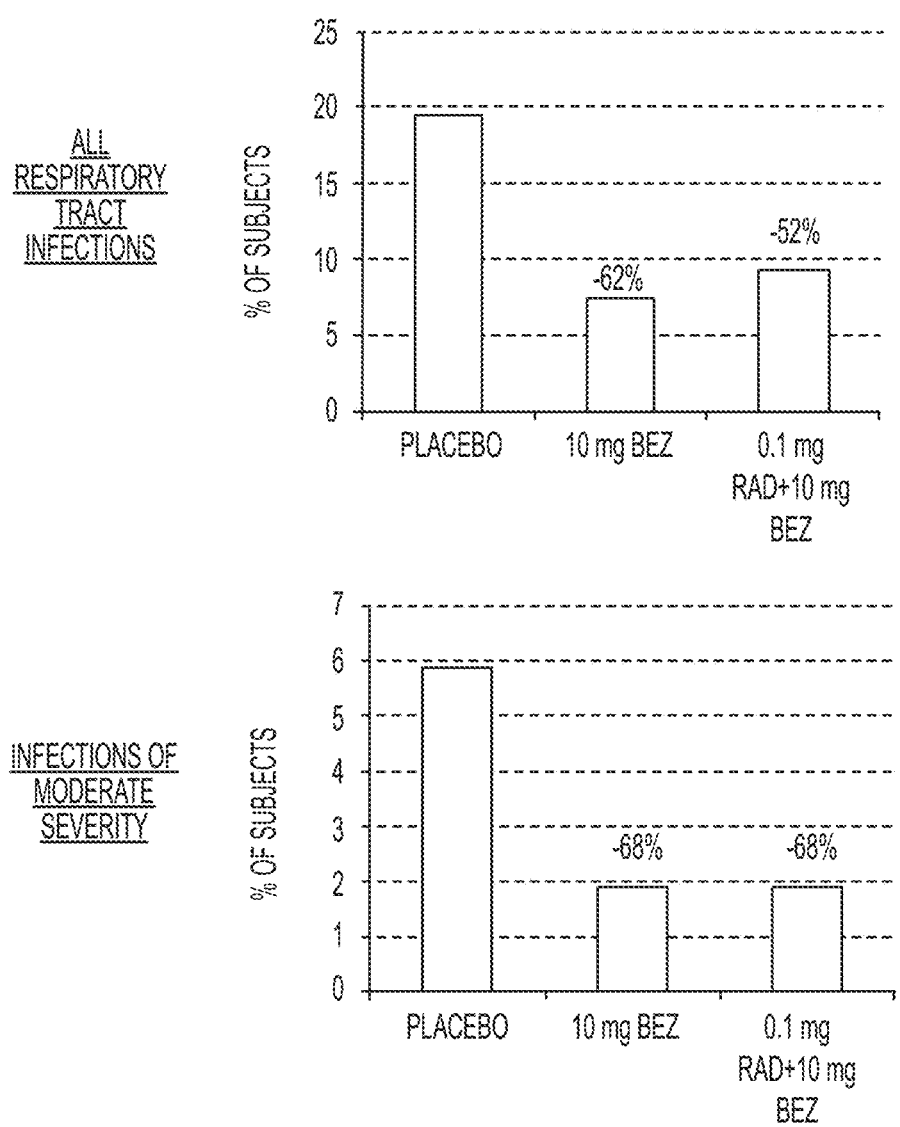
FIG. 2 shows BEZ235 alone or in combination with RAD001 decreases the incidence and severity of respiratory tract infection during the 6 weeks subjects were treated with study drug. BEZ235 alone or in combination with RAD001 decreases the incidence and severity of respiratory tract infection during the 6 weeks subjects were treated with study drug. (Top) The percentage of subjects in each cohort who reported having one or more respiratory tract infections during the 6 weeks they were treated with study drug is shown. (Bottom) The percentage of subjects who experienced respiratory tract infections of moderate severity during the 6 weeks they were treated with study drug is shown. No subjects in the study experienced respiratory tract infections that were assessed as severe. The numbers on top of each bar indicate the percent change relative to placebo.

The rate of infections during the 6 weeks subjects were treated with study drug was also examined. The main infections that occurred during the 6 weeks of study drug treatment were respiratory tract infections. Both BEZ235 and RAD001+BEZ235 led to a reduction in the incidence and severity of respiratory tract infections during the 6 weeks subjects were treated with study drug (FIG. 2).

Figure 3:
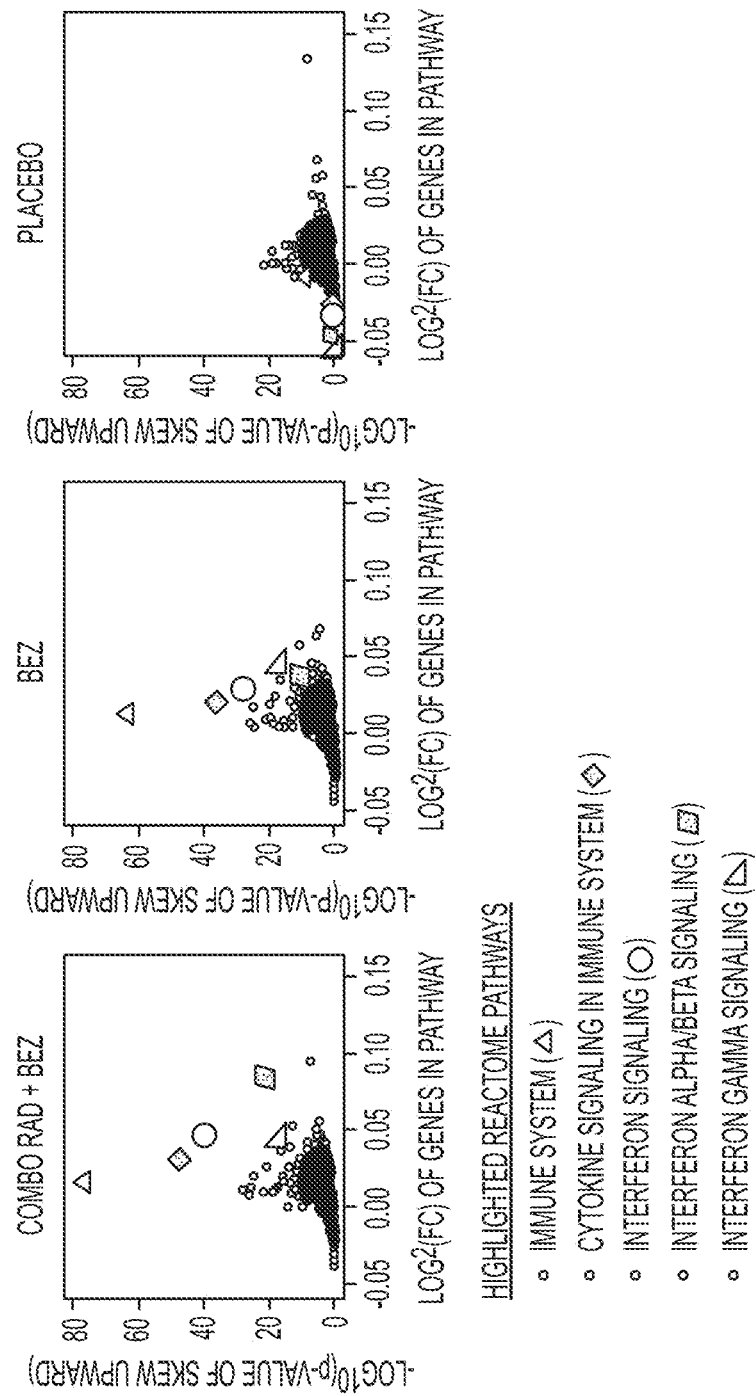
FIG. 3 shows that BEZ235 and RAD001+BEZ235 but not placebo treatment leads to upregulation of immune system and interferon-induced gene expression. Pathway enrichment analysis of gene expression changes in whole blood before versus after 6 weeks of study drug treatment is shown. This analysis revealed a highly significant enrichment of pathways related to immune system and interferon signaling in the BEZ235 monotherapy and BEZ235+RAD001 combination cohort but not in the placebo cohort. The X axis indicates the mean log 2 fold change in expression of genes in each pathway. The y axis indicates the –log 10 of the p value of pathway upregulation, with a value greater than 6 indicating statistical significance with a Bonferroni false discovery rate of less than 0.05. Each dot represents a specific biological pathway.

To explore the possible mechanisms by which the combination of low dose BEZ235 monotherapy or RAD001+BEZ235 combination therapy reduced infection rates in the elderly, RNAseq gene expression profiling was performed in whole blood obtained from subjects at baseline and after 6 weeks of either placebo, BEZ235 or RAD001+BEZ235 treatment. RNAseq analysis of whole blood revealed a highly significant enrichment of pathways related to interferon signaling (FIG. 3). Some of the genes whose expression was most highly upregulated in the enriched pathways included a subset of Type 1 interferon-induced genes (ISGs) that play a critical role in the immune response to viruses (Table 4) (2). These findings suggest that upregulation of a subset of immune system and interferon-induced genes by low dose BEZ235 and/or BEZ235+RAD001 combination therapy enhance immune function and thereby reduce infection rates in the elderly.

Gene Expression Profiling by RNASeq

Peripheral venous blood samples were collected into PAXgene Blood RNA tubes. Total RNA was purified from PAXgene collected blood and the quality and yield of the isolated RNA assessed using an Agilent 2100 Bioanalyzer (Agilent Technologies, Santa Clara, Calif., USA). RNA-Seq libraries were prepared from the RNA using the Illumina TruSeq Stranded Total RNA with the Ribo-Zero Globin Kit. This kit performed the removal of ribosomal RNA and globin mRNA in a single step. The obtained libraries were sequenced using the Illumina HiSeq2500 platform in paired-end mode to a read length of 2×76 base-pairs (bp). Images from the instrument were processed using the manufacturer's software to generate FASTQ sequence files.

Read quality was assessed by running FastQC (version 0.10) on the FASTQ files. Sequencing reads showed excellent quality, with a mean Phred score higher than 30 for all base positions. An average of 100 million 76 bp paired-end reads per sample were mapped to the *Homo sapiens* genome (version GRCh38) and RefSeq UCSC was used for human gene and transcript annotation. An in-house gene quantification pipeline was used to determine the number of counts mapping to each gene (Schuierer, S. & Roma, G. The exon quantification pipeline (EQP): a comprehensive approach to the quantification of gene, exon and junction expression from RNA-seq data. Nucleic acids research (2016)). On average, 88% of the total reads were mapped to the genome or the transcripts, and 30% of the aligned reads mapped to expressed sequences. Samples with less than eight million expressed reads were removed from further analysis, as well as three samples demonstrating a strand imbalance.

RNASeq Differential Gene Expression Analysis

Any gene with an average expression of less than one count per million in any treatment/time condition was considered undetectable and removed from further analysis. Count data for remaining genes was then normalized in R Statistical Computing Software (v3.1.3) using the voom normalization procedure located in the limma package (Law, C W, Chen, Y, Shi, W, and Smyth, G K (2014). Voom: precision weights unlock linear model analysis tools for RNA-seq read counts. Genome Biology 15, R29).

When evaluating the technical quality of the data, we performed a principle component analysis using the prcomp function in R. This analysis indicated that the first principle component reflected multiple aspects of sample processing (RNA extraction batch, yield of mRNA, etc). Thus, we included the value of this principle component as an adjustment for technical variation in subsequent analysis.

For each gene, the following linear mixed model was fit to the voom-normalized expression data, adjusting for relevant covariates (age, gender, and BMI) as well as PC1 using SAS v9.3 software.

proc mixed data=exprsData anovaf;
class SubjID Day Trt Gender;
model log 2exprs=Day Trt Day*Trt PCI Age Gender Bmi/solution DDFM=KenwardRoger;
repeated Day/type=un subject=SubjID;
by gene;

where log 2exprs refers to the voom-normalized expression measurement; Day refers to the timepoint the sample was taken (pre- or post-dose); Trt refers to the treatment group of the subject; PC1 refers to the value of PC1 for that sample; Age refers to the age of the subject; Gender refers to the sex of the subject; Bmi refers to the body mass index of the subject; and SubjID refers to the ID of the subject. Differential expression fold changes and p-values were obtained using the SAS estimate statement. This analysis resulted in gene expression response signatures for each of the treatment arms (BEZ, RAD+BEZ, and Placebo). These gene expression signatures consisted of the post-vs pre-treatment fold change and p-values for each treatment.

RNASeq Gene Expression Pathway Enrichment Analysis

For this analysis, we looked for up- or down-regulated skew of genes in defined biological pathways within each treatment response signature. Canonical pathways (c2.cp.v5.0.entrez.gmt) were downloaded from the canonical signatures database (http://software.broadinstitute.org/gsea/msigdb/). Signatures were defined as described in the "RNASeq Differential Expression Analysis" section. For each pathway and treatment response signature, a weighted KS test was performed as previously described (Subramanian et al. Gene set enrichment analysis: A knowledge-based approach for interpreting genome-wide expression profiles. Proc. Nat. Acad. Sci. vol 102. no 43. 15545-15550 2005) and the resulting −log 10 (p-values) are plotted as a function of mean fold change of the genes in the pathway in FIG. 3.

RNASeq Gene Expression—Designation of Up-Regulated Genes

Genes were considered up-regulated if their fold change was determined to be an outlier using the Tukey method of outlier detection. Specifically, an up-regulated gene met the following criteria: log 2(FC post-vs. pre-treatment) greater than Q3+1.5*(Q3−Q1) where Q3 is the upper (i.e. third) quartile and Q1 the lower (i.e. first) quartile of log 2(FC) for each treatment.

TABLE 4

Upregulated pathway genes in the BEZ235 monotherapy and BEZ235 + RAD001 combination therapy cohorts

| Treatment | Pathway | Mean FC Genes In Pathway | p-Value of Up-regulation Skew | Up-regulated genes |
|---|---|---|---|---|
| Bez | REACTOME_INTERFERON_GAMMA_SIGNALING | 0.04 | 1e−15.8 | FCGR1A; FCGR1B; HLA-DQA2 |
| Bez | REACTOME_INTERFERON_ALPHA_BETA_SIGNALING | 0.03 | 1.00E−11 | IFITM3 |
| Bez | REACTOME_INTERFERON_SIGNALING | 0.03 | 1e−26.5 | IFITM3; FCGR1A; FCGR1B, HLA-DQA2 |
| Bez | REACTOME_IMMUNE_SYSTEM | 0.01 | 1e−54.1 | IFITM3; LILRB4; TRIM9; FCGR1A; FCGR1B; CD274; HLA-DQA2; RAP1GAP; TLR5; C1QA; C1QB; C3; C4BPA; PDCD1LG2; KLHL13; CD80; CDK1 |
| Bez | REACTOME_CYTOKINE_SIGNALING_IN_IMMUNE_SYSTEM | 0.02 | 1e−36.1 | IFITM3; FCGR1A; FCGR1B; HLA-DQA2; CDK1 |
| Comb | REACTOME_INTERFERON_GAMMA_SIGNALING | 0.05 | 1e−16.4 | GBP5; GBP6; FCGR1A; FCGR1B; GBP1; GBP2; HLA-DRB5; IRF7; OAS3; PML; STAT1; OASL; SOCS3 |
| Comb | REACTOME_INTERFERON_ALPHA_BETA_SIGNALING | 0.09 | 1e−21.8 | IFITM3; IFI6; GBP2; IFI27; IFIT2; IFIT1; IFIT3, IRF7; MX1; OAS3; XAF1; STAT1; STAT2; OASL; SOCS3; ISG15 |
| Comb | REACTOME_INTERFERON_SIGNALING | 0.04 | 1e−39.9 | IFITM3; GBP5; GBP6; FCGR1A; FCGR1B; DDX58; IFI6; GBP1; GBP2; HLA-DRB5; IFI27; IFIT2; IFIT1: IFIT3; IRF7; MX1; OAS3; HERC5; PML; XAF1; EIF2AK2; STAT1; STAT2; OASL; SOCS3; UBE2L6; ISG15 |
| Comb | REACTOME_IMMUNE_SYSTEM | 0.02 | 1e−77.5 | IFITM3; TRIM9; GBP5; GBP6; FCGR1A; FCGR1B; RNF182; FOXO3; DDX5B; KIF4A; IFI6; GBP1; GBP2; UBE2S; CD274; HLA-DRB5; IFI27; IFIT2; IFIT1; IFIT3; IL1RN; IRF7; MX1; OAS3; HERC5; PML; XAF1; PPP2R5B; EIF2AK2; RAP1GAP; S100B; STAT1; STAT2; UBE2B; RILP; OASL; SOCS3; UBE2L6; AIM2; KIF23; ISG15; CDK1; MRC2; CDC34 |
| Comb | REACTOME_CYTOKINE_SIGNALING_IN_IMMUNE_SYSTEM | 0.03 | 1e−48.5 | IFITM3; GBP5; GBP6; FCGR1A; FCGR1B; DDX58; IFI6; GBP1; GBP2; HLA-DRB5; IFI27; IFIT2; IFIT1; IFIT3; IL1RN; IRF7; MX1; OAS3; HERC5; PML; XAF1; EIF2AK2; STAT1; STAT2; OASL; SOCS3; UBE2L6; ISG15; CDK1 |

The finding that BEZ235 monotherapy did not improve the response to influenza vaccination but did decrease infection rates was entirely unexpected. Influenza vaccination response is a readout of antigen-specific adaptive immunity. Thus, these findings suggest that BEZ235, unlike RAD001, does not improve the immune response to specific antigens. Instead, BEZ235, as well as the combination of BEZ235+RAD001, may reduce infection rates by improving the non-antigen-specific innate immune response to multiple pathogens via upregulation of ISG expression.

Example 2: RAD001+BEZ235 May have Greater Efficacy than Either RAD001 or BEZ235 Monotherapy for Improving Vaccination Response in the Elderly (an Aging-Related Endpoint) Because the Combination Results in More Selective and Complete TORC1 Inhibition than Either Monotherapy Aging may be due to perturbations of a discreet set of cell signaling pathways including the mTOR pathway. mTOR signals via two complexes: TORC1 and TORC2. Many of the beneficial effects of mTOR inhibition on aging in pre-clinical species may be mediated by inhibition of TORC1 (3,4). In contrast, TORC2 inhibition has been associated with hyperglycemia, hypercholesterolemia and with decreased lifespan in male mice (4,5). In addition, several long-lived animal models have increased rather than decreased TORC2 activity (6). Therefore TORC1-specific inhibition may be optimal for the treatment of aging-related conditions in humans such as declining immune function. Rapalogs such as RAD001 are a class of allosteric mTOR inhibitors that consistently inhibit only the S6K node downstream of the TORC1 complex (7). Low concentrations of BEZ235 such as were achieved in serum of elderly subjects dosed with 10 mg BEZ235 daily (approximately 10-20 nM) also consistently inhibit only the S6K node downstream of TORC1 (8). At higher doses, BEZ235 completely inhibits TORC1, but also inhibits TORC2 (8,9). However, low doses of catalytic inhibitors in combination with low doses of RAD001 synergistically inhibit most if not all nodes downstream of TORC1 without inhibiting TORC2 activity (8,10). Our clinical findings suggest that more complete and selective TORC1 inhibition achieved with a combination of low dose RAD001 and BEZ235 is associated with better enhancement of influenza vaccine response in elderly subjects than low dose RAD001 or BEZ235 monotherapy. A combination of low dose RAD001 and BEZ235 also may have better efficacy for other aging-related conditions than RAD001 and/or BEZ235 monotherapy due to the more complete and selective TORC1 inhibition of the combination.

Example 3: BEZ235 or BEZ235+RAD001 can be Used to Safely Enhance Immune Function and Decrease Infection Rates in the Elderly Via Low Level Upregulation of a Subset of Interferon-Induced Genes (ISGs)

The magnitude of ISG upregulation in whole blood after BEZ235 monotherapy or RAD001+BEZ235 combination treatment was small (1-9%). A low level increase in ISG expression may be sufficient to enhance immune function and decrease infection rates in the elderly while avoiding the undesirable adverse events that occur in patients treated with interferon who have a much larger increase in ISG induction (11). Thus, it is believed that low level ISG induction avoids the safety and tolerability issues associated with high level ISG induction in patients treated with interferon therapy.

Example 4: A 6 Week Course of BEZ235 or BEZ235+RAD001 Leads to Persistent Improvements in Immune Function after Drug Discontinuation BEZ235 monotherapy and the combination of RAD001+ BEZ235 led to a significant reduction in overall infection rates for a year despite the fact that study drug was discontinued after 6 weeks of treatment. The results suggest that mTOR inhibitor therapy may lead to persistent improvements in immune function for months after drug discontinuation. Short courses of the mTOR inhibitor rapamycin have also been shown to extend lifespan in mice, supporting the concept that the beneficial effects of transient mTOR inhibition persisted for months after drug discontinuation (12, 13).

Figure 4:
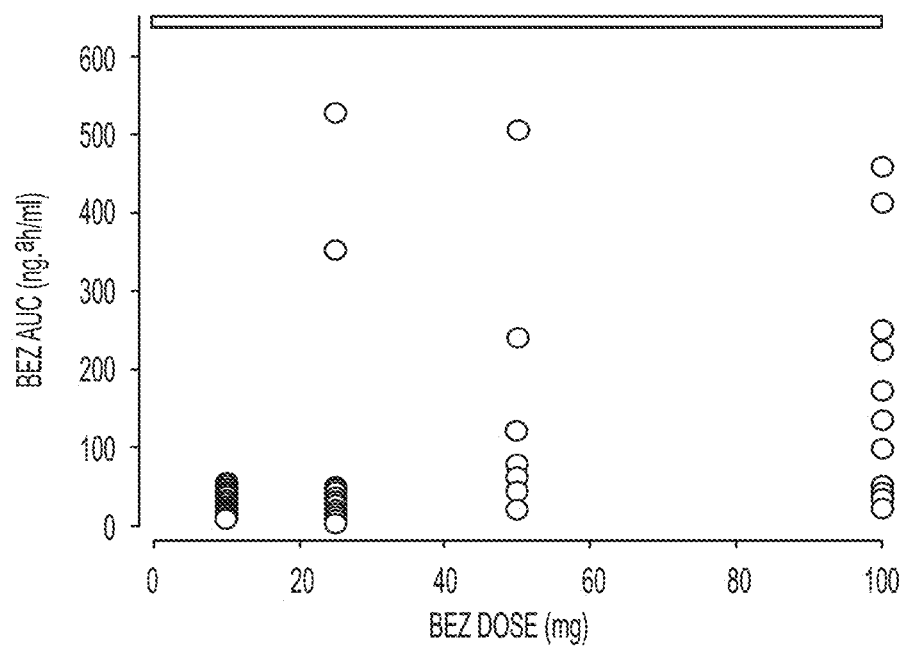
FIG. 4 shows that BEZ235 has unacceptably high PK variability at doses above 10 mg. Dose (mg) vs AUClast are shown. Each dot represents the BEZ235 AUC last on either day 1 or day 8 of dosing for each individual patient in each cohort.

Example 5: PK Variability of BEZ235 can be Mitigated Via the Administration of Low Doses BEZ235 was developed as a dual PI3K-mTOR catalytic inhibitor for oncology indications. However, high doses of BEZ235 used for oncology indications (up to the maximum tolerated dose of 1200 mg daily) were associated with unacceptably high inter-patient variability (AUCtau,ss percent coefficient of variation (% CV)=113%). The PK variability may be due in part to the low solubility of BEZ235 above pH 3. However, the inter-patient variability of BEZ235 10 mg daily was acceptable (AUClast,ss % CV=39%) perhaps because low doses of BEZ235 are able to be completely absorbed in the low pH of the stomach. Increasing PK variability of BEZ235 at doses above 10 mg daily is shown in FIG. 4.

Example 6: BEZ235 Alone or in Combination with RAD001 May have Broad Anti-Aging Effects Via Upregulation of Extracellular Matrix Remodeling Proteins Extracellular matrix remodelling is a common mechanism underlying a diverse set of anti-aging interventions (14). These findings suggest that lack of turnover of the extracellular matrix contributes to aging, and that agents that promote extracellular matrix remodeling may have beneficial effects on aging-related conditions. Serum proteomics suggest that BEZ235 monotherapy or BEZ235+RAD001 combination therapy promote extracellular matrix remodeling. Serum samples were obtained from elderly subjects at baseline or after 6 weeks of treatment with placebo, BEZ235 10 mg daily, or the combination of BEZ235 10 mg daily+ RAD001 0.1 mg daily. Both 6 weeks of BEZ235 monotherapy or the combination of BEZ235+RAD001 but not placebo led to a highly significant upregulation (neg log 10 p value of 14.34 for BEZ235 and 13.32 for BEZ235+ RAD001 combination) in the expression of proteins involved in extracellular matrix disassembly/remodeling (FIG. 5). These findings suggest that BEZ235 monotherapy or the combination of BEZ235+RAD001 may have broad anti-aging effects by stimulating the remodeling of the extracellular matrix. BEZ235 monotherapy or the combination of BEZ235+RAD001 may be particularly efficacious in the treatment of aging-related conditions associated with aging-associated abnormalities in the extracellular matrix of tissues including heart failure, chronic renal failure and skin aging.

Example 7: BEZ235 Alone or in Combination with RAD001 May Decrease Respiratory Tract Infections (RTIs) in Elderly Subjects In the US, pneumonia and influenza are the 5th leading cause of death in people aged 85 and over (National Vital Statistics Report, Deaths, Final Data for 2014, 2016). Moreover, respiratory viruses (for which currently there are no effective treatments) cause the majority of community acquired pneumonias in this population (Jain et al 2015). In addition, 7% of people ≥85 years of age in the US go to the emergency room with RTIs each year (Goto et al 2016). Finally, hospitalizations for RTIs increase the risk of subjects age ≥85 getting admitted to a nursing home. In the US, only 10% of people age 85-95 reside in a nursing home, but 36% of subjects ≥85 years who are hospitalized get discharged to a nursing home (The Older Population 2010 US Census Briefs, National Center for Health Statistics Data Brief 2015).

Prevention of RTIs are also an unmet medical need for elderly subject ≥65 years of age with underlying risk factors such as chronic obstructive pulmonary disease (COPD), asthma, chronic bronchitis, type 2 diabetes mellitus (T2DM), congestive heart failure (CHF), and current smoking. For instance, RTIs are the most common cause of COPD and asthma exacerbations (Nicholson et al BMJ, 2003; Sethi et al 2008). RTIs are also the underlying cause of 16% of hospital admissions in patients with congestive heart failure (Chin and Goldman 1997). Patients with T2DM also are at increased risk of lower respiratory tract infections (Muller et al 2005) and have an increased risk of hospitalization with pneumonia (Kornum et al 2008). Current smoking also increases the risk of developing community acquired pneumonia (Almirall et al 1999). Finally, elderly subjects who have previously had pneumonia are at increased risk for recurrent pneumonia (Hedlund et al 1992).

Accordingly, the purpose of this study is to evaluate the efficacy, tolerability and safety of BEZ235 alone or in combination with RAD001 to support dose selection for further development to reduce the incidence of RTIs in elderly subjects at increased risk of RTI-related morbidity or mortality.

We will determine if low dose mTOR inhibitors decrease the incidence and severity of RTIs in high risk elderly populations defined as age ≥85 years or age ≥65 years who are current smokers, have underlying COPD, asthma, chronic bronchitis, CHF, and/or T2DM, and/or who have been admitted to the hospital or gone to an emergency room with a RTI in the past 12 months.

Objectives and Related Endpoints

TABLE 5

Objectives and related Endpoints

| Objectives | Endpoints |
| --- | --- |
| Primary Objective<br>    To assess the dose-response relationship of 2 different doses of BEZ235 alone or in combination with RAD001 as measured by the percent of elderly subjects experiencing one or more RTIs as compared to placebo during 16 weeks of treatment. | Endpoint for Primary Objective<br>    The percentage of subjects who develop one or more RTIs through Week 16 as assessed by pre-specified diagnostic criteria |
| Secondary Objectives<br>    To assess the safety and tolerability of 2 different doses of BEZ235 alone or in combination with RAD001 in elderly subjects<br>    To evaluate the efficacy of BEZ235 alone or in combination with RAD001 compared to placebo in reducing the incidence of RTIs for 24 weeks<br>    To evaluate the efficacy of BEZ235 alone or in combination with RAD001 compared to placebo at decreasing the incidence of laboratory-confirmed viral RTIs for 16 weeks.<br>    To evaluate the pharmacokinetics (PK) of 2 different doses of BEZ235 given alone or in combination with RAD001 | Endpoints for Secondary Objectives<br>    All safety endpoints (including adverse events and safety laboratories) up until and including 8 weeks post dose.<br>    The percentage of subjects who develop one or more RTIs through Week 24 as assessed by prespecified clinical diagnostic criteria<br>    Incidence of laboratory-confirmed viral RTIs through Week 16 as assessed by respiratory virus PCR of nasopharyngeal swabs<br>    To determine whether covariates e.g., body size, age, gender, race, organ function) affect systemic exposure to BEZ225 and whether these covariates should be used to adjust dosing in future studies. |
| Exploratory Objectives<br>    To explore the effect of BEZ235 alone or in combination with RAD001 compared to placebo on the incidence of RTIs in each of the following subsets of elderly subjects:<br>        ≥85 years of age,<br>        ≥65 year of age with:<br>            Asthma or<br>            COPD or chronic bronchitis or<br>            T2DM or<br>            CHF or<br>            Current smoker or<br>            Emergency room visit or hospitalization for RTI within past 12 months<br>    To explore the effect of BEZ235 alone or in combination with RAD001 compared to placebo on total infection rates for 16 or 24 weeks<br>    To explore the effect of BEZ235 alone or in combination with RAD001 compared to placebo on urinary tract infection (UTI) rates for 16 or 24 weeks<br>    To explore the effect of BEZ235 alone or in combination with RAD001 compared to placebo at decreasing the severity or duration of upper respiratory tract infection symptoms in the subset of subjects who develop upper respiratory tract infections<br>    To explore the effect of BEZ235 alone or in combination with RAD001 on the response to influenza vaccination in the subset of subjects who receive influenza vaccination as part of their routine health care during the study<br>    To explore the effect of BEZ235 alone or in combination with RAD001 compared to placebo on health care resource utilization for infections<br>    To explore the effect of BEZ235 alone or in combination with RAD001 compared to placebo on improvement in physical function as assessed by the 6 minute walk test (6WMT) | Endpoints for Exploratory Objectives<br>    Percentage of subjects in each subgroup who develop one or more RTIs through Weeks 16 and 24 as assessed by prespecified clinical diagnostic criteria<br>    Total number of infections per person through Week 16 or Week 24 as assessed by prespecified clinical diagnostic criteria<br>    Total number of UTIs per person through Week 16 or Week 24 as assessed by prespecified clinical diagnostic criteria<br>    Severity and duration of upper respiratory tract symptoms as assessed by the short Wisconsin Upper Respiratory Symptom Survey (WURSS-21)<br>    Change in hemagglutination inhibition (HI) geometric mean titer (GMT) from baseline to 4 weeks post influenza vaccination<br>    Number of visits to a health care provider for symptoms related to infections; total number of CXRs done to evaluate infections, total number of antibiotics prescribed for infections; total number of visits to the ED for infections; and total number of hospitalizations for infections through Week 16 or 24 of the study as assessed by review of medical records<br>    Change from baseline to Week 16 in 6 MWT<br>    Change from baseline to Week 16 in grip strength as assessed by a dynamometer<br>    Change from baseline to Week 16 in cardiac function as assessed by echocardiogram.<br>    Change from baseline to Week 16 in perception of breathlessness as assessed by a questionnaire administered before and after a 6 MWT<br>    Change from baseline to Week 16 in gene expression in whole blood and in soluble biomarkers in serum |

TABLE 5-continued

Objectives and related Endpoints

| Objectives | Endpoints |
|---|---|
| To explore the effect of BEZ235 alone or in combination with RAD001 compared to placebo on grip strength | |
| To explore the effect of BEZ235 alone or in combination with RAD001 compared to placebo on cardiac function | |
| To explore the effect of BEZ235 alone or in combination with RAD001 as compared to placebo on the perception of breathlessness | |
| To explore the effect of BEZ235 alone or in combination with RAD001 compared to placebo on gene expression and circulating biomarkers in blood | |

Study Design

This is a 24 week randomized, blinded, placebo-controlled, parallel-group, dose finding 2-stage adaptive design study to assess the safety, tolerability and efficacy of two doses of BEZ235 alone or in combination with RAD001 as compared to placebo in elderly subjects without unstable medical conditions. Subjects can be included if they are at increased risk of a respiratory tract infection as defined by being either ≥85 years of age or ≥65 years of age and a current smoker, or with underlying COPD, asthma, chronic bronchitis, T2DM, or CHF and/or have been hospitalized or evaluated in an emergency room in the past year for a RTI. The study will be composed of a 6 week screening period, a 4 week run-in period, 16-week treatment period and an 8 week follow-up period Study Periods:

The total planned duration of the study for each subject is up to 24 weeks from randomization to the last follow up visit (FIG. 3-1); study treatment is taken for 16 weeks.

Screening Period:

During the screening visit (maximum 6 weeks prior to baseline/randomization), subjects will be assessed for eligibility to participate in the trial based on inclusion/exclusion criteria.

Run-in Period:

During the run-in period (maximum 4 weeks prior to baseline/randomization), subjects who meet the eligibility criteria during the screening visit will be enrolled in the study and will come into the clinic and undergo a hand grip strength test and 6-minute walk test (6MWT) in order to familiarize the subjects with this test and thereby reduce test variability at the baseline visit. Subjects will also be administered a breathlessness questionnaire before and after a 6 MWT. In addition, during the run-in period subjects will undergo baseline echocardiography to assess cardiac function.

Blinded Treatment Phase:

Part 1 (to be conducted in either the southern or northern hemisphere)

Treatment Phase (16 Weeks):

At the baseline visit (Visit 3), eligible subjects will be randomized to 1 of 3 treatment groups in a ratio of 1:1:1

(1) BEZ235 5 mg daily (2) BEZ235 10 mg daily (3) Matching placebo daily

Subjects will be treated for 16 weeks with study drug. Approximately 56 subjects will be enrolled in each treatment group for a total enrollment of approximately 168 subjects. It is assumed that there will be approximately a 10% drop-out rate, resulting in approximately 150 subjects completing Part 1 of the study (approximately 50 subjects in each arm). If the drop-out rate is higher than 10%, replacements may be enrolled.

At the baseline visit, subjects will undergo clinical evaluation and have blood drawn for baseline safety assessments, EAST (IgE levels) and biomarker assessments. Subjects who have not yet received their seasonal influenza vaccine will have influenza titers drawn. Subjects will also undergo grip strength, 6MWT and complete a breathlessness questionnaire before and after the 6 MWT at the baseline visit. Subjects will then be given their first dose of study drug in the clinic and sent home with study drug. Subjects will also be sent home from the baseline visit with a diary. Subjects will be instructed to record the time and number of capsules of study medication administered at home each day in the diary. Subjects will also be instructed to record any infections symptoms that occur between visits in the diary. Finally, subjects will also be sent home with the short Wisconsin Upper Respiratory Symptom Survey (WURSS-21) that they will be instructed to fill out daily if they develop symptoms of an upper respiratory tract infection until their symptoms resolve.

After subjects have taken study drug for 1 week, a telephone call between the subjects and the site should take place to confirm that the first week of study drug was well tolerated. If study drug is not tolerated during the first week of study drug treatment, the investigator may discontinue study drug after discussion with the resTORbio Medical Monitor.

Provided the study drug continues to be well tolerated, subjects will be treated with study drug for 16 weeks, during which time they will return to the clinic every 2 weeks (visits week 2, 4, 6 and 8) for the first 8 weeks, and then every 4 weeks (visit week 12 and 16) for the final 8 weeks to have clinical evaluations and blood drawn for safety assessments. Blood will also be drawn for PK assessments at the week 4, 6, and 8 visits. Blood will be drawn for biomarker assessments at baseline and the week 6, 16 and 24 visits. Sites will contact subjects twice weekly during the study either by phone or at the site visits to confirm that the subjects are taking the study drug as instructed and that the study drug continues to be well tolerated. Sites will also administer a Respiratory Tract Infection Questionnaire during each contact and instruct subjects who develop 2 or more respiratory tract infection symptoms or 1 or more non-respiratory tract infection symptoms to come in for an unscheduled visit as soon as possible so that they can be evaluated by the Investigator.

Subjects who come to the site for an unscheduled visit due to infection symptoms will be evaluated by Investigators who will capture relevant signs and symptoms of the infection on an Infection Investigator Worksheet as described in the Study Operations Manual. Subjects who have symptoms of a RTI will have a nasopharyngeal swab taken in the clinic. If subjects are unable or unwilling to return to the site for an unscheduled visit, the Investigator can call the subject and complete the Infection Investigator Worksheet by phone and obtain the nasopharyngeal swab when the subject comes in for their next visit. Appropriate medical care will be provided for all infections. Subjects who require additional medical care should be referred to their healthcare provider or to a hospital if indicated.

Subjects who receive a seasonal influenza vaccine as part of their routine health care during the study will be asked to return to the site for an unscheduled visit approximately 4 weeks after their influenza vaccination to have influenza titers drawn.

After 16 weeks of study drug treatment, subjects will have blood taken for safety labs and biomarker assessments, and will undergo repeat grip strength assessment, 6MWT, and will complete a breathlessness questionnaire before and after the 6MWT at the Week 16 visit. Subjects will also have a repeat echocardiogram after completing 16 weeks of study drug treatment.

Post Treatment Follow-Up Period (8 Weeks):

All subjects will be followed up for 8 weeks after their last dose of study drug, during which time they will be told to continue to record any infections that occur in their diaries. Sites will continue to call subjects twice weekly and administer the Twice Weekly Contact for Respiratory Symptoms Questionnaire. Subjects who develop 2 or more respiratory tract infection symptoms or 1 or more non-respiratory tract infection symptoms will be instructed to come in for an unscheduled visit as soon as possible so that they can be evaluated by the Investigator as described above. Subjects with respiratory tract infection symptoms will have a nasopharyngeal swab taken for respiratory virus PCR. Further details are provided in the Study Operations Manual.

At the end of study Week 24 Visit, subjects will undergo a complete physical exam and have blood taken for safety labs and biomarker assessments, and will undergo repeat grip strength assessment, 6MWT, and will complete a breathlessness questionnaire before and after the 6MWT.

At or after the Week 24 visit, the investigator will review the subjects' medical records to determine if additional infections occurred that were not captured in the study database. Information about infections that had not been captured will be recorded on the appropriate Investigator Infection Worksheet.

Patients who develop medically important laboratory abnormalities or medically important AEs that are considered related to study drug and which are not resolved or stabilized at the end of the follow-up period will be followed, beyond the planned post treatment follow-up period, until these events have resolved or stabilized. If at the time of the completion of the study, these events are unresolved, they should be captured as "ongoing" in the database.

Interim Analysis (IA):

An IA will be performed when at least 120 subjects randomized in Part 1 have completed the Week 16 visit. An un-blinded Data Monitoring Committee (DMC) will review the results of the IA and make recommendations for the study. Possible decisions at the interim analysis are:

whether to stop the study the BEZ235 monotherapy dosing arms for futility, or continue with 1 or 2 BEZ235 treatment arms in Part 2;

whether to resize the study based on the rate of respiratory tract infections during Part 1;

whether to change the duration of treatment based on safety data and respiratory tract infection rate data from Part 1; and/or whether additional PK sampling is needed and/or if the PK sampling regimen can be simplified.

Part 2 (to be Conducted in the Opposite Hemisphere from Part 1):

In Part 2, between 310-430 subjects who meet the eligibility criteria during the screening visit will be enrolled in the study. These subjects will be randomized to placebo, 0, 1 or 2 doses of BEZ235 from Part 1, and 5 mg or 10 mg BEZ235+RAD001 0.1 mg. Procedures identical to those in Part 1 will apply during the screening, run-in, treatment and post treatment follow-up periods in Part 2.

FIG. 3-1 Study Design:

TABLE 1

| Part 1 |
|---|
| BEZ235  5 mg daily |
| BEZ235 10 mg daily |
| Placebo |

| Randomization ↑ | | Primary endpoint ↑ |
|---|---|---|
| Screening | Double-Blind Treatment | Follow-up |
| 6 weeks | 16 weeks | 8 weeks |
| Run-in 4 weeks | | |

TABLE 2

| Part 2 |
|---|
| BEZ235 dose(s) chosen from Part 1 |
| BEZ235 + RAD001 0.1 mg daily |
| Placebo |

| Randomization ↑ | | Primary endpoint ↑ |
|---|---|---|
| Screening | Double-Blind Treatment | Follow-up |
| 6 weeks | 16 weeks | 8 weeks |
| Run-in 4 weeks | | |

Rationale for Study Design:

The study is designed as a standard randomized, blinded placebo-controlled, parallel-group study to obtain efficacy, tolerability and safety data in an unbiased fashion and determine the dose-response characteristics of the investigated drugs. A run-in period is included to obtain baseline echocardiograms and to familiarize subjects with the 6MWT and hand grip strength assessments. Sixteen weeks of treatment in Parts 1 and 2 are considered sufficient to result in a clinically meaningful reduction in RTIs during winter cold and flu season in each hemisphere. The last 8 weeks of the study will provide information about whether the reduction in RTIs persists after subjects have discontinued study drug treatment. PK samples will be obtained in all subjects at the week 4, 6, and 8 visits to enable characterization of PK after the study drugs have reached steady state levels.

Study Population:

Data from two previous clinical trials conducted by Novartis (CRAD002X2202 and CBEZ235Y2201) suggests that 6 weeks of treatment of elderly subjects ≥65 years of age with low doses of BEZ235 and/or RAD001 was safe and decreased the incidence of RTIs. The risk/benefit of BEZ235 alone or in combination with RAD001 may be most favorable in elderly subjects who are at increased risk of RTI-related morbidity and mortality. Therefore, in the current study we will enroll elderly subjects who are considered at increased risk of RTI-related morbidity and mortality as defined by having one of the following conditions:

Age>=85
Age>=65 years with:
Asthma
COPD Gold Class I or II
    Postbronchodialator $FEV_1/FVC<0.70$ and $FEV_1 \geq 50\%$ predicted
Chronic bronchitis
T2DM
CHF New York Heart Association functional classification I-II
    No symptoms or mild symptoms (shortness of breath and/or angina) and slight limitation during ordinary activity
Current smoker
One or more emergency room visits or hospitalizations for a RTI during the previous 12 months Further Inclusion Criteria:

Females must be post-menopausal. Women are considered post-menopausal and not of child bearing potential if they have had 12 months of natural (spontaneous) amenorrhea with an appropriate clinical profile (e.g. age appropriate, history of vasomotor symptoms) or have had surgical bilateral oophorectomy (with or without hysterectomy), total hysterectomy or tubal ligation at least six weeks ago. In the case of oophorectomy alone, only when the reproductive status of the woman has been confirmed by follow up hormone level assessment is she considered not of child bearing potential.

Sexually active male subjects with a partner of childbearing potential must be willing to wear a condom while on study drug and for 1 week after stopping study drug, and should not father a child in this period. A condom is required to be used also by vasectomized men in order to prevent delivery of the drug via seminal fluid.

At screening and baseline, vital signs (systolic and diastolic blood pressure, pulse rate and respiratory rate) will be assessed in a sitting position after the subject has rested for at least three (3) minutes. Sitting vital signs should be within the following ranges:

Oral or tympanic body temperature between 35.0-37.5° C.
systolic blood pressure, 90-160 mm Hg
diastolic blood pressure, 50-95 mm Hg
pulse rate, 40-95 bpm If vital signs are outside these ranges, the Investigator may obtain up to two additional readings, so that up to 3 consecutive assessments are made. At least the last set of readings must be within the ranges provided above in order for the subject to qualify.

Subjects must weigh at least 40 kg.

Subject must be able to communicate well with the investigator, and to understand and comply with the requirements of the study.

Results of a study may be quantified using different methods. For instance, results may be quantified by looking at the rate of infection during a particular time period as calculated by dividing the total number of infections by the total number of subjects. Alternatively, results of a study may be quantified by looking at the percentage of subjects having one or more infections during a particular time period.

Primary Endpoint:

The primary endpoint of the study is a decrease in the percentage of subjects who experience one or more RTIs during the 16 weeks of study drug treatment because RTIs cause significant morbidity and mortality in the elderly (Millett et al 2013).

Secondary Endpoints:

As secondary endpoint, the percentage of subjects who experience one or more RTIs for 24 weeks (16 weeks on study drug treatment followed by 8 weeks off study drug treatment) will be assessed to determine if elderly subjects continue to have a reduced rate of respiratory tract infections after study drug discontinuation.

Since most respiratory tract infections in the elderly are caused by viruses (Jain et al 2015), the effect of BEZ235 alone or in combination with RAD001 on the incidence of laboratory-confirmed viral respiratory tract infections (as determined by respiratory virus PCR of nasopharyngeal swabs) will be assessed during the 16 weeks subjects are receiving study drug.

As an additional secondary endpoint, the pharmacokinetics (PK) of BEZ235 given alone or in combination with RAD001 will be evaluated.

Exploratory Endpoints:

As an exploratory endpoint, the effect of BEZ235 alone or in combination with RAD001 on the incidence of RTIs will be explored in specific subsets of the elderly to determine if the efficacy varies between subgroups.

The effect of BEZ235 alone or in combination with RAD001 as compared to placebo on the incidence of all infections as well as the incidence of UTIs from baseline to Week 16 or 24 will also be explored because in clinical trial CBEZ235Y2201, elderly subjects treated for 6 weeks with either BEZ235 10 mg daily or a combination of BEZ235 10 mg plus RAD001 0.1 mg daily had a significant decrease in the rate of all infections as well as a decrease in the rate UTIs over the year following study drug administration.

As an additional exploratory endpoint, the effect of BEZ235 alone or in combination with RAD001 as compared to placebo on the duration and/or severity of upper respiratory tract symptoms will be assessed using the WURSS-21 survey.

Results of CBEZ235Y2201 indicated that the response of elderly volunteers to influenza vaccination was enhanced when they received a 6 week course of low dose BEZ235 in combination with RAD001 two weeks prior to receiving the influenza vaccine. Therefore as an exploratory endpoint, the effect of BEZ235 alone or in combination with RAD001 as compared to placebo on the response to influenza vaccination will be assessed in subjects who receive an influenza vaccine as part of their routine health care during the study.

mTOR inhibition by BEZ235 alone or in combination with RAD001 may have anti-aging effects beyond just improving immune function and decreasing infection rates. In our previous clinical trial, a subset of subjects treated for 6 weeks with a combination of BEZ235 10 mg and RAD001 0.1 mg daily, but not subjects treated with placebo, spontaneously reported an increase in energy while on study drug. In addition, old mice treated with the mTOR inhibitor rapamycin have been noted to have increased physical activity and/or grip strength as compared to placebo-treated controls (Flynn et al 2013). Therefore as an additional exploratory endpoint, we will assess whether BEZ235 alone or in combination with RAD001 increases grip strength and/or endurance as assessed by a 6MWT.

mTOR inhibitors have also been reported to improve cardiac function, in old mice (Flynn et al 2013). Therefore as additional exploratory endpoints, we will determine if BEZ235 alone or in combination with RAD001 as compared to placebo improves cardiac function as assessed by echocardiography at Week 16 relative to baseline.

As a final exploratory endpoint, the effects of BEZ235 alone or in combination with RAD001 on gene expression in whole blood and on serum proteomics will be assessed to further elucidate the mechanisms by which BEZ235 alone or in combination with RAD001 may improve immune function and/or impact aging biology.

Rationale for Dose/Regimen, Route of Administration and Duration of Treatment:

In Novartis clinical study CBEZ235Y2201, all mTOR inhibitor dosing regimens (BEZ235 10 mg daily, RAD001 0.5 mg or 0.1 mg daily, and BEZ235 10 mg daily plus RAD001 0.1 mg daily) were well tolerated and reduced the incidence of respiratory tract infections by between 50-60% during the 6 weeks elderly subjects received study drug treatment. In addition, the combination of BEZ235 10 mg and RAD001 0.1 mg daily significantly improved the response to influenza vaccination. In the current study we will extend these findings and determine if BEZ235 alone or in combination with RAD001 decreases the incidence of respiratory tract infections when elderly subjects are treated for a longer 16 week duration during winter cold and flu season in each hemisphere when respiratory tract infection rates are the highest. We will also investigate the minimum efficacious dose level for BEZ235 by comparing the safety and efficacy of BEZ235 5 mg vs 10 mg daily. BEZ235 10 mg daily was chosen as a dose in the current study because it was associated with a reduction in both respiratory tract infections and total infections in clinical study CBEZ235Y2201. BEZ235 5 mg daily is predicted by modeling and simulation to inhibit S6K phosphorylation by only 10% and therefore may be sub-therapeutic and may establish the minimally efficacious dose in the current study. We will test doses of BEZ235 above 10 mg up to BEZ235 10 mg twice daily, because PK variability of BEZ235 in previously clinical studies was high at doses of 25 mg and above. Accordingly, certain dosing regimens contemplated herein comprise administration of, e.g., 10 mg BEZ235 twice a day. In some such embodiments, a dosing regimen comprises administration of, e.g., 10 mg BEZ235 twice a day either alone (i.e., without RAD001) or in combination with RAD001, for instance in combination with a daily dose of 0.1 mg RAD001. In some embodiments, dosing regimens contemplated herein comprise administering daily an amount of RAD001 ranging from about 0.015 mg to about 0.1 mg. In some such embodiments, an amount of RAD001 ranging from about 0.015 mg to about 0.1 mg is administered in combination with an amount of BEZ235.

REFERENCES

1. Iob, A. et al. Evidence of increased clinical protection of an MF59-adjuvant influenza vaccine compared to a non-adjuvant vaccine among elderly residents of long-term care facilities in Italy, Epidemiol. Infect. 133, 687-693 (2005).
2. McNab F, Mayer-Barber K, Sher A, Wack A, O'Garra A. Type I interferons in infectious disease. Nat Rev Immunol. 2015 February; 15(2):87-103. doi: 10.1038/nri3787. Review.
3. Laplante M & Sabatini D M. mTOR signaling in growth control and disease. Cell. 149, 274-93 (2012).
4. Lamming D W, et al. Rapamycin-induced insulin resistance is mediated by mTORC2 loss and uncoupled from longevity. Science 335 1638-43 (2012).
5. Lamming D W, et al. Depletion of Rictor, an essential protein component of mTORC2, decreases male lifespan. Aging Cell. 13, 911-7 (2014).
6. Dominick G, Berryman D E, List E O, Kopchick J J, Li X, Miller R A, Garcia G G. Regulation of mTOR activity in Snell dwarf and GH receptor gene-disrupted mice. Endocrinology. 2015 February; 156(2):565-75. doi: 10.1210/en.2014-1690. Epub 2014 Dec. 2.
7. Feldman M E, Apsel B, Uotila A, Loewith R, Knight Z A, Ruggero D, Shokat K M. Active-site inhibitors of mTOR target rapamycin-resistant outputs of mTORC1 and mTORC2. PLoS Biol. 2009 Feb. 10; 7(2):e38.
8. Nyfeler B, Chen Y, Li X, Pinzon-Ortiz M, Wang Z, Reddy A, Pradhan E, Das R, Lehár J, Schlegel R, Finan P M, Cao Z A, Murphy L O, Huang A. RAD001 enhances the potency of BEZ235 to inhibit mTOR signaling and tumor growth. PLoS One. 2012; 7(11):e48548. doi: 10.1371/journal.pone.0048548. Epub 2012 Nov. 14.
9. Serra V, Markman B, Scaltriti M, Eichhorn P J, Valero V, Guzman M, Botero M L, Llonch E, Atzori F, Di Cosimo S, Maira M, Garcia-Echeverria C, Parra J L, Arribas J, Baselga J. NVP-BEZ235, a dual PI3K/mTOR inhibitor, prevents PI3K signaling and inhibits the growth of cancer cells with activating PI3K mutations. Cancer Res. 2008 Oct. 1; 68(19):8022-30. doi: 10.1158/0008-5472.CAN-08-1385.
10. Nyfeler B, Bergman P, Triantafellow E, Wilson C J, Zhu Y, Radetich B, Finan P M, Klionsky D J, Murphy L O. Relieving autophagy and 4EBP1 from rapamycin resistance. Mol Cell Biol. 2011 July; 31(14):2867-76. doi: 10.1128/MCB.05430-11. Epub 2011 May 16.
11. Harari D, Orr I, Rotkopf R, Baranzini S E, Schreiber G. A robust type I interferon gene signature from blood RNA defines quantitative but not qualitative differences between three major IFNβ drugs in the treatment of multiple sclerosis. Hum Mol Genet. 2015 Jun. 1; 24(11): 3192-205. doi: 10.1093/hmg/ddv071.
12. Bitto A, Ito T K, Pineda V V, LeTexier N J, Huang H Z, Sutlief E, Tung H, Vizzini N, Chen B, Smith K, Meza D, Yajima M, Beyer R P, Kerr K F, Davis D J, Gillespie C H, Snyder J M, Treuting P M, Kaeberlein M. Transient rapamycin treatment can increase lifespan and healthspan in middle-aged mice. Elife. 2016 Aug. 23; 5. pii: e16351. doi: 10.7554/eLife.16351.
13. C. Chen, Y. Liu, Y. Liu, P. Zheng. mTOR regulation and therapeutic rejuvenation of aging hematopoietic stem cells, Sci. Signal. 2, ra75 (2009).

14. Ewald C Y, Landis J N, Porter Abate J, Murphy C T, Blackwell T K. Dauer-independent insulin/IGF-1-signalling implicates collagen remodelling in longevity. Nature. 2015 Mar. 5; 519(7541):97-101.

Enumerated Embodiments

In a first embodiment, the invention is a method comprising the step of administering (a) a low dose of RAD001 or a pharmaceutically acceptable salt thereof; (b) a low dose of BEZ235 or a pharmaceutically acceptable salt thereof; or (c) a combination thereof to a patient, wherein the patient experiences fewer illnesses due to infection than a patient not administered RAD001 or a pharmaceutically acceptable salt thereof, BEZ235 or a pharmaceutically acceptable salt thereof, or a combination thereof.

In a second embodiment, the invention is a method according to the first embodiment, wherein the patient's innate immunity is enhanced.

In a third embodiment, the invention is a method according to the first or second embodiment, wherein antigen-specific immunity is not enhanced.

In a fourth embodiment, the invention is a method according to the second embodiment, wherein at least one interferon-inducing gene (ISG) is upregulated.

In a fifth embodiment, the invention is a method according to any one of the first through fourth embodiments, wherein the infection is a urinary tract infection; or an infection of the teeth or gums.

In a sixth embodiment, the invention is a method according to any one of the first through fourth embodiments, wherein the infection is a respiratory tract infection.

In a seventh embodiment, the invention is a method according to any one of the first through fourth embodiments, wherein the infection is a viral infection.

In an eighth embodiment, the invention is a method according to any one of the first through seventh embodiments, wherein the patient is elderly.

In a ninth embodiment, the invention is a method according to any one of the first through eighth embodiments, wherein the patient is at least 65 years old.

In a tenth embodiment, the invention is a method according to any one of the first through ninth embodiments, wherein the patient is at least 75 years old; or at least 85 years old.

In an eleventh embodiment, the invention is a method according to any one of the first through tenth embodiments, wherein the low dose of RAD001 or a pharmaceutically acceptable salt thereof, the low dose of BEZ235 or a pharmaceutically acceptable salt thereof, or combination thereof, is administered to the patient for up to about 6 consecutive weeks.

In a twelfth embodiment, the invention is a method according to the eleventh embodiment, wherein the patient continues to experience fewer illnesses due to infection from about 1 day until about 1 year after the administration of the RAD001 or a pharmaceutically acceptable salt thereof, the BEZ235 or a pharmaceutically acceptable salt thereof, or combination thereof.

In a thirteenth embodiment, the invention is a method according to the eleventh embodiment, wherein the patient continues to experience fewer illnesses due to infection for at least 1 month and until about 1 year after the administration of the RAD001 or a pharmaceutically acceptable salt thereof, the BEZ235 or a pharmaceutically acceptable salt thereof, or combination thereof.

In a fourteenth embodiment, the invention is a method according to the eleventh embodiment, wherein the patient continues to experience fewer illnesses due to infection for at least 3 months and until about 1 year after the administration of the RAD001 or a pharmaceutically acceptable salt thereof, the BEZ235 or a pharmaceutically acceptable salt thereof, or combination thereof.

In a fifteenth embodiment, the invention is a method according to the eleventh embodiment, wherein the patient continues to experience fewer illnesses due to infection for at least 6 months after the administration of the RAD001 or a pharmaceutically acceptable salt thereof, the BEZ235 or a pharmaceutically acceptable salt thereof, or combination thereof.

In a sixteenth embodiment, the invention is a method according to any one of the first through fifteenth embodiments, wherein the patient is administered the low dose of BEZ235 or a pharmaceutically acceptable salt thereof as a monotherapy.

In a seventeenth embodiment, the invention is a method according to any one of the first through fifteenth embodiments, wherein the patient is administered the low dose of RAD001 or a pharmaceutically acceptable salt thereof as a monotherapy.

In an eighteenth embodiment, the invention is a method according to any one of the first through fifteenth embodiments, wherein the patient is administered both the low dose of RAD001 or a pharmaceutically acceptable salt thereof and the low dose of BEZ235 or a pharmaceutically acceptable salt thereof as a combination therapy.

In a nineteenth embodiment, the invention is a method according to any one of the first through sixteenth or eighteenth embodiments, wherein the pharmacokinetic AUC variability of patients receiving the low dose of BEZ235 or a pharmaceutically acceptable salt thereof is lower than a patient receiving a higher dose of BEZ235 or a pharmaceutically acceptable salt thereof.

In a twentieth embodiment, the invention is a method according to any one of the first through fifteenth, seventeenth, or eighteenth embodiments, wherein RAD001 or a pharmaceutically acceptable salt thereof is in the neutral form.

In a twenty-first embodiment, the invention is a method according to any one of the first through sixteenth or eighteenth embodiments, wherein BEZ235 or a pharmaceutically acceptable salt thereof is the monotosylate salt.

In a twenty-second embodiment, the invention is a method according to any one of the first through fifteenth or seventeenth through twenty-first embodiments, comprising the administration of 0.01-0.2 mg of RAD001 or a pharmaceutically acceptable salt thereof.

In a twenty-third embodiment, the invention is a method according to any one of the first through sixteenth or eighteenth through twenty-second embodiments, comprising the administration of 1-50 mg of BEZ235 or a pharmaceutically acceptable salt thereof.

In a twenty-fourth embodiment, the invention is a method according to any one of the first through twenty-third embodiments, wherein the subject is immunocompromised.

In a twenty-fifth embodiment, the invention is a method according to any one of the first through twenty-fourth embodiments, wherein the subject has an impaired immune response.

In a twenty-sixth embodiment, the invention is a method according to any one of the first through twenty-fifth embodiments, wherein the subject is immunosenescent.

In a twenty-seventh embodiment, the invention is a method of upregulating at least one interferon-inducing gene (ISG), comprising administering (a) a low dose of RAD001 or a pharmaceutically acceptable salt thereof; (b) a low dose of BEZ235 or a pharmaceutically acceptable salt thereof or (c) a combination thereof, to a patient.

In a twenty-eighth embodiment, the invention is a method of upregulating at least one protein involved in extracellular matrix remodeling, comprising administering (a) a low dose of RAD001 or a pharmaceutically acceptable salt thereof; (b) a low dose of BEZ235 or a pharmaceutically acceptable salt thereof; or (c) a combination thereof, to a patient.

In a twenty-ninth embodiment, the invention is the method of the twenty-eighth embodiment, wherein the protein involved in extracellular matrix remodeling is significantly upregulated following treatment for at least about 1 week; at least about 2 weeks; at least about 3 weeks; or at least about 6 weeks.

In a thirtieth embodiment, the invention is a method of treating a disease or condition associated with aberrant extracellular matrix remodeling, comprising administering (a) a low dose of RAD001 or a pharmaceutically acceptable salt thereof (b) a low dose of BEZ235 or a pharmaceutically acceptable salt thereof; or (c) a combination thereof, to a patient.

In a thirty-first embodiment, the invention is the method of the thirtieth embodiment, wherein the disease or condition associated with aberrant extracellular matrix remodeling is selected from heart failure, heart failure with preserved ejection fraction, chronic renal failure, glomerunephropathy, skin aging, NASH, hepatitis fibrosis/cirrhosis, pulmonary fibrosis including idiopathic pulmonary fibrosis, aging-related tendon dysfunction/stiffening, arthritis including osteoarthritis, sarcopenia, myelofibrosis, myelodysplasia, aging-related dysfunction of the blood brain barrier, diabetic nephropathy, atherosclerosis, or wound healing.

We claim:

1. A method of upregulating at least one interferon-inducing gene (ISG), comprising administering daily as a monotherapy about 8-12 mg of BEZ235 or a pharmaceutically acceptable salt thereof to a patient, thereby upregulating the at least one interferon-inducing gene (ISG) in the patient.

2. The method according to claim 1, wherein the patient's innate immunity is enhanced.

3. The method according to claim 2, wherein antigen-specific immunity is not enhanced.

4. The method according to claim 2, wherein the patient experiences fewer illnesses due to infection than a patient not administered BEZ235 or a pharmaceutically acceptable salt thereof.

5. The method according to claim 4, wherein the infection is a urinary tract infection.

6. The method according to claim 4, wherein the infection is a respiratory tract infection.

7. The method according to claim 4, wherein the infection is an oral infection including a periodontal infection.

8. The method according to claim 4, wherein the infection is a viral infection.

9. The method according to claim 1, wherein the patient is elderly.

10. The method according to claim 1, wherein the patient is asthmatic.

11. The method according to claim 1, wherein the patient is at least 65 years old.

12. The method according to claim 10, wherein the patient is at least 65 years old.

13. The method according to claim 1, wherein the patient is at least 75 years old.

14. The method according to claim 1, wherein the patient is at least 85 years old.

15. The method according to claim 1, wherein the pharmacokinetic AUK variability of patients receiving the BEZ235 or a pharmaceutically acceptable salt thereof is lower than a patient receiving a higher dose of BEZ235 or a pharmaceutically acceptable salt thereof.

16. The method according to claim 1, wherein the BEZ235 or pharmaceutically acceptable salt thereof is the monotosylate salt.

17. The method according to claim 1, wherein the subject is immunocompromised.

18. The method according to claim 1, wherein the subject has an impaired immune response.

19. The method according to claim 1, wherein the subject is immunosenescent.

20. The method according to claim 1, wherein the BEZ235 or pharmaceutically acceptable salt thereof is administered daily to the patient for up to about 16 consecutive weeks.

21. The method according to claim 1, wherein about 9-11 mg of BEZ235 or pharmaceutically acceptable salt thereof is administered daily.

22. The method according to claim 21, wherein about 10 mg of BEZ235 or pharmaceutically acceptable salt thereof is administered daily.

23. The method according to claim 5, wherein the BEZ235 or pharmaceutically acceptable salt thereof is administered twice per day.

24. The method according to claim 5, wherein the BEZ235 or pharmaceutically acceptable salt thereof is administered once per day.

* * * * *